(12) United States Patent
Ernst et al.

(10) Patent No.: US 9,138,175 B2
(45) Date of Patent: *Sep. 22, 2015

(54) MOTION TRACKING SYSTEM FOR REAL TIME ADAPTIVE IMAGING AND SPECTROSCOPY

(71) Applicants: THE QUEEN'S MEDICAL CENTER, Honolulu, HI (US); THE UNIVERSITY OF HAWAII, Honolulu, HI (US); THE MEDICAL COLLEGE OF WISCONSIN, INC., Milwaukee, WI (US); UWM RESEARCH FOUNDATION, INC., Milwaukee, WI (US)

(72) Inventors: Thomas Michael Ernst, Honolulu, HI (US); Thomas Edmund Prieto, Grafton, WI (US); Brian Stewart Randall Armstrong, Shorewood, WI (US)

(73) Assignees: The Queen's Medical Center, Honolulu, HI (US); The University of Hawaii, Honolulu, HI (US); The Medical College of Wisconsin, Inc., Milwaukee, WI (US); UWM Research Foundation, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/698,350

(22) Filed: Apr. 28, 2015

(65) Prior Publication Data

US 2015/0227793 A1   Aug. 13, 2015

Related U.S. Application Data

(63) Continuation of application No. 14/034,252, filed on Sep. 23, 2013, now Pat. No. 9,076,212, which is a continuation of application No. 13/735,907, filed on Jan. 7, 2013, now Pat. No. 8,571,293, which is a continuation of application No. 13/338,166, filed on Dec. 27, 2011, now Pat. No. 8,374,411, which is a continuation of application No. 11/804,417, filed on May 18, 2007, now Pat. No. 8,121,361.

(60) Provisional application No. 60/802,216, filed on May 19, 2006.

(51) Int. Cl.
| | |
|---|---|
| *A61B 5/11* | (2006.01) |
| *G06K 9/00* | (2006.01) |
| *G06T 7/00* | (2006.01) |
| *H04N 7/18* | (2006.01) |
| *A61B 6/04* | (2006.01) |
| *A61B 5/00* | (2006.01) |
| *A61B 6/00* | (2006.01) |

(52) U.S. Cl.
CPC ............. *A61B 5/1127* (2013.01); *A61B 5/1128* (2013.01); *A61B 5/721* (2013.01); *A61B 6/0492* (2013.01); *A61B 6/547* (2013.01); *G06K 9/00624* (2013.01); *G06T 7/0012* (2013.01); *H04N 7/18* (2013.01)

(58) Field of Classification Search
CPC ...... A61B 5/1127; A61B 5/1128; A61B 5/11; A61B 6/0492; A61B 5/721; A61B 5/7292; A61B 6/547; A61B 2019/5255; A61B 2019/5265; G01R 33/28; G01R 33/56509; G06T 7/004; G06T 7/0012; G06T 2207/20201; H04N 5/23264; G06K 2009/3291; G06K 2017/0045
See application file for complete search history.

(56) References Cited

U.S. PATENT DOCUMENTS

| | | |
|---|---|---|
| 4,724,386 A | 2/1988 | Haacke et al. |
| 4,894,129 A | 1/1990 | Leiponen et al. |
| 4,953,554 A | 9/1990 | Zerhouni et al. |
| 5,318,026 A | 6/1994 | Pelc |
| 5,545,993 A | 8/1996 | Taguchi et al. |
| 5,615,677 A | 4/1997 | Pelc et al. |
| 5,687,725 A | 11/1997 | Wendt |
| 5,886,257 A | 3/1999 | Gustafson et al. |
| 5,889,505 A | 3/1999 | Toyama |
| 5,936,722 A | 8/1999 | Armstrong et al. |
| 5,936,723 A | 8/1999 | Schmidt et al. |

| Patent No. | Date | Inventor |
|---|---|---|
| 5,947,900 A | 9/1999 | Derbyshire et al. |
| 5,987,349 A | 11/1999 | Schulz |
| 6,044,308 A | 3/2000 | Huissoon |
| 6,057,680 A | 5/2000 | Foo et al. |
| 6,061,644 A | 5/2000 | Leis |
| 6,088,482 A | 7/2000 | He |
| 6,144,875 A | 11/2000 | Schweikard et al. |
| 6,236,737 B1 | 5/2001 | Gregson et al. |
| 6,246,900 B1 | 6/2001 | Cosman et al. |
| 6,279,579 B1 | 8/2001 | Riaziat et al. |
| 6,285,902 B1 | 9/2001 | Kienzle, III et al. |
| 6,292,683 B1 | 9/2001 | Gupta et al. |
| 6,298,262 B1 | 10/2001 | Franck et al. |
| 6,381,485 B1 | 4/2002 | Hunter et al. |
| 6,384,908 B1 | 5/2002 | Schmidt et al. |
| 6,390,982 B1 | 5/2002 | Bova et al. |
| 6,402,762 B2 | 6/2002 | Hunter et al. |
| 6,405,072 B1 | 6/2002 | Cosman |
| 6,467,905 B1 | 10/2002 | Stahl et al. |
| 6,484,131 B1 | 11/2002 | Amorai-Moriya et al. |
| 6,490,475 B1 | 12/2002 | Seeley et al. |
| 6,501,981 B1 * | 12/2002 | Schweikard et al. ......... 600/427 |
| 6,621,889 B1 | 9/2003 | Mostafavi |
| 6,650,920 B2 | 11/2003 | Schaldach et al. |
| 6,662,036 B2 | 12/2003 | Cosman |
| 6,687,528 B2 | 2/2004 | Gupta et al. |
| 6,690,965 B1 | 2/2004 | Riaziat et al. |
| 6,711,431 B2 | 3/2004 | Sarin et al. |
| 6,731,970 B2 | 5/2004 | Schlossbauer et al. |
| 6,758,218 B2 | 7/2004 | Anthony |
| 6,771,997 B2 | 8/2004 | Schaffer |
| 6,794,869 B2 | 9/2004 | Brittain |
| 6,856,827 B2 | 2/2005 | Seeley et al. |
| 6,856,828 B2 | 2/2005 | Cossette et al. |
| 6,876,198 B2 | 4/2005 | Watanabe et al. |
| 6,891,374 B2 | 5/2005 | Brittain |
| 6,892,089 B1 | 5/2005 | Prince et al. |
| 6,897,655 B2 | 5/2005 | Brittain et al. |
| 6,913,603 B2 | 7/2005 | Knopp et al. |
| 6,937,696 B1 | 8/2005 | Mostafavi |
| 6,959,266 B1 | 10/2005 | Mostafavi |
| 6,973,202 B2 | 12/2005 | Mostafavi |
| 6,980,679 B2 | 12/2005 | Jeung et al. |
| 7,007,699 B2 | 3/2006 | Martinelli et al. |
| 7,107,091 B2 | 9/2006 | Jutras et al. |
| 7,110,805 B2 | 9/2006 | Machida |
| 7,123,758 B2 | 10/2006 | Jeung et al. |
| 7,171,257 B2 | 1/2007 | Thomson |
| 7,191,100 B2 | 3/2007 | Mostafavi |
| 7,204,254 B2 | 4/2007 | Riaziat et al. |
| 7,209,777 B2 | 4/2007 | Saranathan et al. |
| 7,209,977 B2 | 4/2007 | Acharya et al. |
| 7,260,253 B2 | 8/2007 | Rahn et al. |
| 7,260,426 B2 | 8/2007 | Schweikard et al. |
| 7,295,007 B2 | 11/2007 | Dold |
| 7,313,430 B2 | 12/2007 | Urquhart et al. |
| 7,327,865 B2 | 2/2008 | Fu et al. |
| 7,348,776 B1 | 3/2008 | Aksoy et al. |
| 7,403,638 B2 | 7/2008 | Jeung et al. |
| 7,498,811 B2 | 3/2009 | Macfarlane et al. |
| 7,505,805 B2 | 3/2009 | Kuroda |
| 7,535,411 B2 | 5/2009 | Falco |
| 7,551,089 B2 | 6/2009 | Sawyer |
| 7,561,909 B1 | 7/2009 | Pai et al. |
| 7,567,697 B2 | 7/2009 | Mostafavi |
| 7,602,301 B1 | 10/2009 | Stirling et al. |
| 7,603,155 B2 | 10/2009 | Jensen |
| 7,623,623 B2 | 11/2009 | Raanes et al. |
| 7,657,300 B2 | 2/2010 | Hunter et al. |
| 7,657,301 B2 | 2/2010 | Mate et al. |
| 7,659,521 B2 | 2/2010 | Pedroni |
| 7,660,623 B2 | 2/2010 | Hunter et al. |
| 7,668,288 B2 | 2/2010 | Conwell et al. |
| 7,689,263 B1 | 3/2010 | Fung et al. |
| 7,715,604 B2 | 5/2010 | Sun et al. |
| 7,742,077 B2 | 6/2010 | Sablak et al. |
| 7,742,621 B2 | 6/2010 | Hammoud et al. |
| 7,742,804 B2 | 6/2010 | Faul et al. |
| 7,744,528 B2 | 6/2010 | Wallace et al. |
| 7,760,908 B2 | 7/2010 | Curtner et al. |
| 7,766,837 B2 | 8/2010 | Pedrizzetti et al. |
| 7,769,430 B2 | 8/2010 | Mostafavi |
| 7,772,569 B2 | 8/2010 | Bewersdorf et al. |
| 7,787,011 B2 | 8/2010 | Zhou et al. |
| 7,791,808 B2 | 9/2010 | French et al. |
| 7,792,249 B2 | 9/2010 | Gertner et al. |
| 7,796,154 B2 | 9/2010 | Senior et al. |
| 7,798,730 B2 | 9/2010 | Westerweck |
| 7,801,330 B2 | 9/2010 | Zhang et al. |
| 7,805,987 B1 | 10/2010 | Smith |
| 7,806,604 B2 | 10/2010 | Bazakos et al. |
| 7,817,046 B2 | 10/2010 | Coveley et al. |
| 7,817,824 B2 | 10/2010 | Liang et al. |
| 7,819,818 B2 | 10/2010 | Ghajar |
| 7,833,221 B2 | 11/2010 | Voegele |
| 7,834,846 B1 | 11/2010 | Bell |
| 7,835,783 B1 | 11/2010 | Aletras |
| 7,839,551 B2 | 11/2010 | Lee et al. |
| 7,840,253 B2 | 11/2010 | Tremblay et al. |
| 7,844,320 B2 | 11/2010 | Shahidi |
| 7,850,526 B2 | 12/2010 | Zalewski et al. |
| 7,860,301 B2 | 12/2010 | Se et al. |
| 7,866,818 B2 | 1/2011 | Schroeder et al. |
| 7,868,282 B2 | 1/2011 | Lee et al. |
| 7,878,652 B2 | 2/2011 | Chen et al. |
| 7,883,415 B2 | 2/2011 | Larsen et al. |
| 7,889,907 B2 | 2/2011 | Engelbart et al. |
| 7,894,877 B2 | 2/2011 | Lewin et al. |
| 7,902,825 B2 | 3/2011 | Bammer et al. |
| 7,907,987 B2 | 3/2011 | Dempsey |
| 7,908,060 B2 | 3/2011 | Basson et al. |
| 7,908,233 B2 | 3/2011 | Angell et al. |
| 7,911,207 B2 | 3/2011 | Macfarlane et al. |
| 7,912,532 B2 | 3/2011 | Schmidt et al. |
| 7,920,250 B2 | 4/2011 | Robert et al. |
| 7,920,911 B2 | 4/2011 | Hoshino et al. |
| 7,925,066 B2 | 4/2011 | Ruohonen et al. |
| 7,925,549 B2 | 4/2011 | Looney et al. |
| 7,931,370 B2 | 4/2011 | Bartomen |
| 7,944,354 B2 | 5/2011 | Kangas et al. |
| 7,944,454 B2 | 5/2011 | Zhou et al. |
| 7,945,304 B2 | 5/2011 | Feinberg |
| 7,946,921 B2 | 5/2011 | Ofek et al. |
| 7,962,197 B2 | 6/2011 | Rioux et al. |
| 7,971,999 B2 | 7/2011 | Zinser |
| 7,977,942 B2 | 7/2011 | White |
| 7,978,925 B1 | 7/2011 | Souchard |
| 7,988,288 B2 | 8/2011 | Donaldson |
| 7,990,365 B2 | 8/2011 | Marvit et al. |
| 8,005,571 B2 * | 8/2011 | Sutherland et al. ........... 700/248 |
| 8,009,198 B2 | 8/2011 | Alhadef |
| 8,019,170 B2 | 9/2011 | Wang et al. |
| 8,021,231 B2 | 9/2011 | Walker et al. |
| 8,022,982 B2 | 9/2011 | Thorn |
| 8,024,026 B2 | 9/2011 | Groszmann |
| 8,031,909 B2 | 10/2011 | Se et al. |
| 8,031,933 B2 | 10/2011 | Se et al. |
| 8,036,425 B2 | 10/2011 | Hou |
| 8,041,077 B2 | 10/2011 | Bell |
| 8,041,412 B2 | 10/2011 | Glossop et al. |
| 8,048,002 B2 | 11/2011 | Ghajar |
| 8,049,867 B2 | 11/2011 | Bridges et al. |
| 8,055,020 B2 | 11/2011 | Meuter et al. |
| 8,060,185 B2 | 11/2011 | Hunter et al. |
| 8,063,929 B2 | 11/2011 | Kurtz et al. |
| 8,073,197 B2 | 12/2011 | Xu et al. |
| 8,077,914 B1 | 12/2011 | Kaplan |
| 8,085,302 B2 | 12/2011 | Zhang et al. |
| 8,086,026 B2 | 12/2011 | Schulz |
| 8,086,299 B2 | 12/2011 | Adler et al. |
| RE43,147 E | 1/2012 | Aviv |
| 8,094,193 B2 | 1/2012 | Peterson |
| 8,095,209 B2 | 1/2012 | Flaherty |
| 8,098,889 B2 | 1/2012 | Zhu et al. |
| 8,113,991 B2 | 2/2012 | Kutliroff |
| 8,116,527 B2 | 2/2012 | Sabol |
| 8,121,356 B2 | 2/2012 | Friedman |
| 8,121,361 B2 | 2/2012 | Ernst et al. |

| | | | | | | |
|---|---|---|---|---|---|---|
| 8,134,597 B2 | 3/2012 | Thorn | 8,334,900 B2 | 12/2012 | Qu et al. | |
| 8,135,201 B2 | 3/2012 | Smith et al. | 8,339,282 B2 | 12/2012 | Noble | |
| 8,139,029 B2 | 3/2012 | Boillot | 8,351,651 B2 | 1/2013 | Lee | |
| 8,139,896 B1 | 3/2012 | Ahiska | 8,368,586 B2 | 2/2013 | Mohamadi | |
| 8,144,118 B2 | 3/2012 | Hildreth | 8,369,574 B2 | 2/2013 | Atu | |
| 8,144,148 B2 | 3/2012 | El Dokor | 8,374,393 B2 | 2/2013 | Cobb | |
| 8,150,063 B2 | 4/2012 | Chen | 8,374,411 B2 * | 2/2013 | Ernst et al. | 382/128 |
| 8,150,498 B2 | 4/2012 | Gielen et al. | 8,374,674 B2 | 2/2013 | Gertner | |
| 8,160,304 B2 | 4/2012 | Rhoads | 8,376,226 B2 | 2/2013 | Dennard | |
| 8,165,844 B2 | 4/2012 | Luinge et al. | 8,376,827 B2 | 2/2013 | Cammegh | |
| 8,167,802 B2 | 5/2012 | Baba et al. | 8,379,927 B2 | 2/2013 | Taylor | |
| 8,172,573 B2 | 5/2012 | Sonenfeld et al. | 8,380,284 B2 | 2/2013 | Saranathan et al. | |
| 8,175,332 B2 | 5/2012 | Herrington | 8,386,011 B2 | 2/2013 | Wieczorek | |
| 8,179,604 B1 | 5/2012 | Prada Gomez | 8,390,291 B2 | 3/2013 | Macfarlane et al. | |
| 8,180,428 B2 | 5/2012 | Kaiser et al. | 8,390,729 B2 | 3/2013 | Long | |
| 8,180,432 B2 | 5/2012 | Sayeh | 8,395,620 B2 | 3/2013 | El Dokor | |
| 8,187,097 B1 | 5/2012 | Zhang | 8,400,398 B2 | 3/2013 | Schoen | |
| 8,189,869 B2 | 5/2012 | Bell | 8,400,490 B2 | 3/2013 | Apostolopoulos | |
| 8,189,889 B2 | 5/2012 | Pearlstein et al. | 8,405,491 B2 | 3/2013 | Fong | |
| 8,189,926 B2 | 5/2012 | Sharma | 8,405,656 B2 | 3/2013 | El Dokor | |
| 8,190,233 B2 | 5/2012 | Dempsey | 8,405,717 B2 | 3/2013 | Kim | |
| 8,194,134 B2 | 6/2012 | Furukawa | 8,406,845 B2 | 3/2013 | Komistek et al. | |
| 8,195,084 B2 | 6/2012 | Xiao | 8,411,931 B2 | 4/2013 | Zhou | |
| 8,199,983 B2 | 6/2012 | Qureshi | 8,427,538 B2 | 4/2013 | Ahiska | |
| 8,206,219 B2 | 6/2012 | Shum | 8,428,319 B2 | 4/2013 | Tsin et al. | |
| 8,207,967 B1 | 6/2012 | El Dokor | 8,571,293 B2 * | 10/2013 | Ernst et al. | 382/131 |
| 8,208,758 B2 | 6/2012 | Wang | 8,615,127 B2 | 12/2013 | Fitzpatrick | |
| 8,213,693 B1 | 7/2012 | Li | 8,744,154 B2 | 6/2014 | Van Den Brink | |
| 8,214,012 B2 | 7/2012 | Zuccolotto et al. | 2002/0082496 A1 | 6/2002 | Kuth | |
| 8,214,016 B2 | 7/2012 | Lavallee et al. | 2002/0091422 A1 | 7/2002 | Greenberg et al. | |
| 8,216,016 B2 | 7/2012 | Yamagishi et al. | 2002/0115931 A1 | 8/2002 | Strauss et al. | |
| 8,218,818 B2 | 7/2012 | Cobb | 2002/0188194 A1 | 12/2002 | Cosman | |
| 8,218,819 B2 | 7/2012 | Cobb | 2003/0063292 A1 | 4/2003 | Mostafavi | |
| 8,218,825 B2 | 7/2012 | Gordon | 2003/0088177 A1 | 5/2003 | Totterman et al. | |
| 8,221,399 B2 | 7/2012 | Amano | 2003/0116166 A1 | 6/2003 | Anthony | |
| 8,223,147 B1 | 7/2012 | El Dokor | 2004/0071324 A1 | 4/2004 | Norris et al. | |
| 8,224,423 B2 | 7/2012 | Faul | 2004/0116804 A1 | 6/2004 | Mostafavi | |
| 8,226,574 B2 | 7/2012 | Whillock | 2004/0140804 A1 | 7/2004 | Polzin et al. | |
| 8,229,163 B2 | 7/2012 | Coleman | 2004/0171927 A1 | 9/2004 | Lowen et al. | |
| 8,229,166 B2 | 7/2012 | Teng | 2005/0027194 A1 | 2/2005 | Adler et al. | |
| 8,229,184 B2 | 7/2012 | Benkley | 2005/0054910 A1 * | 3/2005 | Tremblay et al. | 600/411 |
| 8,232,872 B2 | 7/2012 | Zeng | 2005/0105772 A1 | 5/2005 | Voronka et al. | |
| 8,235,529 B1 | 8/2012 | Raffle | 2005/0107685 A1 | 5/2005 | Seeber | |
| 8,235,530 B2 | 8/2012 | Maad | 2005/0137475 A1 * | 6/2005 | Dold | 600/414 |
| 8,241,125 B2 | 8/2012 | Hughes | 2005/0283068 A1 | 12/2005 | Zuccolotto et al. | |
| 8,243,136 B2 | 8/2012 | Aota | 2006/0004281 A1 | 1/2006 | Saracen | |
| 8,243,269 B2 | 8/2012 | Matousek | 2006/0045310 A1 | 3/2006 | Tu et al. | |
| 8,243,996 B2 | 8/2012 | Steinberg | 2006/0074292 A1 | 4/2006 | Thomson et al. | |
| 8,248,372 B2 | 8/2012 | Saila | 2006/0241405 A1 | 10/2006 | Leitner et al. | |
| 8,249,691 B2 | 8/2012 | Chase et al. | 2007/0093709 A1 | 4/2007 | Abernathie | |
| 8,253,770 B2 | 8/2012 | Kurtz | 2007/0239169 A1 | 10/2007 | Plaskos et al. | |
| 8,253,774 B2 | 8/2012 | Huitema | 2008/0039713 A1 | 2/2008 | Thomson et al. | |
| 8,253,778 B2 | 8/2012 | Atsushi | 2008/0181358 A1 | 7/2008 | Van Kampen et al. | |
| 8,259,109 B2 | 9/2012 | El Dokor | 2008/0183074 A1 | 7/2008 | Carls et al. | |
| 8,279,288 B2 | 10/2012 | Son | 2008/0212835 A1 | 9/2008 | Tavor | |
| 8,284,157 B2 | 10/2012 | Markovic | 2008/0221442 A1 | 9/2008 | Tolkowsky et al. | |
| 8,284,847 B2 | 10/2012 | Adermann | 2008/0273754 A1 | 11/2008 | Hick et al. | |
| 8,287,373 B2 | 10/2012 | Marx | 2008/0287780 A1 | 11/2008 | Chase et al. | |
| 8,289,390 B2 | 10/2012 | Aggarwal | 2008/0317313 A1 | 12/2008 | Goddard et al. | |
| 8,289,392 B2 | 10/2012 | Williams, Sr. | 2009/0028411 A1 | 1/2009 | Pfeuffer | |
| 8,290,208 B2 | 10/2012 | Kurtz | 2009/0052760 A1 | 2/2009 | Smith et al. | |
| 8,290,229 B2 | 10/2012 | Qureshi | 2009/0185663 A1 | 7/2009 | Gaines, Jr. et al. | |
| 8,301,226 B2 | 10/2012 | Csavoy et al. | 2009/0209846 A1 | 8/2009 | Bammer | |
| 8,306,260 B2 | 11/2012 | Zhu | 2009/0253985 A1 | 10/2009 | Shachar et al. | |
| 8,306,267 B1 | 11/2012 | Gossweiler, III | 2009/0304297 A1 | 12/2009 | Adabala et al. | |
| 8,306,274 B2 | 11/2012 | Grycewicz | 2009/0306499 A1 | 12/2009 | Van Vorhis et al. | |
| 8,306,663 B2 | 11/2012 | Wickham | 2010/0057059 A1 | 3/2010 | Makino | |
| 8,310,656 B2 | 11/2012 | Zalewski | 2010/0069742 A1 | 3/2010 | Partain et al. | |
| 8,310,662 B2 | 11/2012 | Mehr | 2010/0091089 A1 | 4/2010 | Cromwell et al. | |
| 8,311,611 B2 | 11/2012 | Csavoy et al. | 2010/0099981 A1 | 4/2010 | Fishel | |
| 8,314,854 B2 | 11/2012 | Yoon | 2010/0125191 A1 | 5/2010 | Sahin | |
| 8,315,691 B2 | 11/2012 | Sumanaweera et al. | 2010/0137709 A1 | 6/2010 | Gardner et al. | |
| 8,316,324 B2 | 11/2012 | Boillot | 2010/0148774 A1 | 6/2010 | Kamata | |
| 8,320,621 B2 | 11/2012 | McEldowney | 2010/0149099 A1 | 6/2010 | Elias | |
| 8,323,106 B2 | 12/2012 | Zalewski | 2010/0149315 A1 | 6/2010 | Qu | |
| 8,325,228 B2 | 12/2012 | Mariadoss | 2010/0160775 A1 | 6/2010 | Pankratov | |
| 8,330,811 B2 | 12/2012 | Maguire, Jr. | 2010/0164862 A1 | 7/2010 | Sullivan | |
| 8,330,812 B2 | 12/2012 | Maguire, Jr. | 2010/0165293 A1 | 7/2010 | Tanassi et al. | |
| 8,331,019 B2 | 12/2012 | Cheong | 2010/0167246 A1 | 7/2010 | Ghajar | |

| | | | | | |
|---|---|---|---|---|---|
| 2010/0172567 A1 | 7/2010 | Prokoski | 2011/0172521 A1 | 7/2011 | Zdeblick et al. |
| 2010/0177929 A1 | 7/2010 | Kurtz | 2011/0175801 A1 | 7/2011 | Markovic |
| 2010/0178966 A1 | 7/2010 | Suydoux | 2011/0175809 A1 | 7/2011 | Markovic |
| 2010/0179390 A1 | 7/2010 | Davis | 2011/0175810 A1 | 7/2011 | Markovic |
| 2010/0179413 A1 | 7/2010 | Kadour et al. | 2011/0176723 A1 | 7/2011 | Ali et al. |
| 2010/0183196 A1 | 7/2010 | Fu et al. | 2011/0180695 A1 | 7/2011 | Li |
| 2010/0191631 A1 | 7/2010 | Weidmann | 2011/0181893 A1 | 7/2011 | MacFarlane |
| 2010/0194879 A1 | 8/2010 | Pasveer | 2011/0182472 A1 | 7/2011 | Hansen |
| 2010/0198067 A1 | 8/2010 | Mahfouz | 2011/0187640 A1 | 8/2011 | Jacobsen |
| 2010/0198101 A1 | 8/2010 | Song | 2011/0193939 A1 | 8/2011 | Vassigh |
| 2010/0198112 A1 | 8/2010 | Maad | 2011/0199461 A1 | 8/2011 | Horio |
| 2010/0199232 A1 | 8/2010 | Mistry | 2011/0201916 A1 | 8/2011 | Duyn et al. |
| 2010/0210350 A9 | 8/2010 | Walker | 2011/0201939 A1 | 8/2011 | Hubschman et al. |
| 2010/0214267 A1 | 8/2010 | Radivojevic | 2011/0202306 A1 | 8/2011 | Eng |
| 2010/0231511 A1 | 9/2010 | Henty | 2011/0205358 A1 | 8/2011 | Aota |
| 2010/0231692 A1 | 9/2010 | Perlman | 2011/0207089 A1 | 8/2011 | Lagettie |
| 2010/0245536 A1 | 9/2010 | Huitema | 2011/0208437 A1 | 8/2011 | Teicher |
| 2010/0245593 A1 | 9/2010 | Kim | 2011/0216002 A1 | 9/2011 | Weising |
| 2010/0251924 A1 | 10/2010 | Taylor | 2011/0216180 A1 | 9/2011 | Pasini |
| 2010/0253762 A1 | 10/2010 | Cheong | 2011/0221770 A1 | 9/2011 | Kruglick |
| 2010/0268072 A1 | 10/2010 | Hall et al. | 2011/0229862 A1 | 9/2011 | Parikh |
| 2010/0282902 A1 | 11/2010 | Indraeswaran | 2011/0230755 A1 | 9/2011 | MacFarlane et al. |
| 2010/0283833 A1 | 11/2010 | Yeh | 2011/0234807 A1 | 9/2011 | Jones |
| 2010/0284119 A1 | 11/2010 | Coakley | 2011/0234834 A1 | 9/2011 | Sugimoto |
| 2010/0289899 A1 | 11/2010 | Hendron | 2011/0237933 A1 | 9/2011 | Cohen |
| 2010/0290668 A1 | 11/2010 | Friedman | 2011/0242134 A1 | 10/2011 | Miller |
| 2010/0292841 A1 | 11/2010 | Wickham | 2011/0244939 A1 | 10/2011 | Cammegh |
| 2010/0295718 A1 | 11/2010 | Mohamadi | 2011/0250929 A1 | 10/2011 | Lin |
| 2010/0296701 A1 | 11/2010 | Hu | 2011/0251478 A1 | 10/2011 | Wieczorek |
| 2010/0302142 A1 | 12/2010 | French | 2011/0255845 A1 | 10/2011 | Kikuchi |
| 2010/0303289 A1 | 12/2010 | Polzin | 2011/0257566 A1 | 10/2011 | Burdea |
| 2010/0311512 A1 | 12/2010 | Lock | 2011/0260965 A1 | 10/2011 | Kim |
| 2010/0321505 A1 | 12/2010 | Kokubun | 2011/0262002 A1 | 10/2011 | Lee |
| 2010/0328055 A1 | 12/2010 | Fong | 2011/0267427 A1 | 11/2011 | Goh |
| 2010/0328201 A1 | 12/2010 | Marbit | 2011/0267456 A1 | 11/2011 | Adermann |
| 2010/0328267 A1 | 12/2010 | Chen | 2011/0276396 A1 | 11/2011 | Rathod |
| 2010/0330912 A1 | 12/2010 | Saila | 2011/0279663 A1 | 11/2011 | Fan |
| 2011/0001699 A1 | 1/2011 | Jacobsen | 2011/0285622 A1 | 11/2011 | Marti |
| 2011/0006991 A1 | 1/2011 | Elias | 2011/0286010 A1 | 11/2011 | Kusik et al. |
| 2011/0007939 A1 | 1/2011 | Teng | 2011/0291925 A1 | 12/2011 | Israel |
| 2011/0007946 A1 | 1/2011 | Liang | 2011/0293143 A1 | 12/2011 | Narayanan et al. |
| 2011/0008759 A1 | 1/2011 | Usui | 2011/0293146 A1 | 12/2011 | Grycewicz |
| 2011/0015521 A1 | 1/2011 | Faul | 2011/0298708 A1 | 12/2011 | Hsu |
| 2011/0019001 A1 | 1/2011 | Rhoads | 2011/0298824 A1 | 12/2011 | Lee |
| 2011/0025853 A1 | 2/2011 | Richardson | 2011/0300994 A1 | 12/2011 | Verkaaik |
| 2011/0038520 A1 | 2/2011 | Yui | 2011/0301449 A1 | 12/2011 | Maurer, Jr. |
| 2011/0043631 A1 | 2/2011 | Marman | 2011/0301934 A1 | 12/2011 | Tardis |
| 2011/0043759 A1 | 2/2011 | Bushinsky | 2011/0303214 A1 | 12/2011 | Welle |
| 2011/0050562 A1 | 3/2011 | Schoen | 2011/0304541 A1 | 12/2011 | Dalal |
| 2011/0050569 A1 | 3/2011 | Marvit | 2011/0304650 A1 | 12/2011 | Canpillo |
| 2011/0050947 A1 | 3/2011 | Marman | 2011/0304706 A1 | 12/2011 | Porter |
| 2011/0052002 A1 | 3/2011 | Cobb | 2011/0306867 A1 | 12/2011 | Gopinadhan |
| 2011/0052003 A1 | 3/2011 | Cobb | 2011/0310220 A1 | 12/2011 | McEldowney |
| 2011/0052015 A1 | 3/2011 | Saund | 2011/0310226 A1 | 12/2011 | McEldowney |
| 2011/0054870 A1 | 3/2011 | Dariush | 2011/0316994 A1 | 12/2011 | Lemchen |
| 2011/0057816 A1 | 3/2011 | Noble | 2011/0317877 A1 | 12/2011 | Bell |
| 2011/0058020 A1 | 3/2011 | Dieckmann | 2012/0002112 A1 | 1/2012 | Huang |
| 2011/0069207 A1 | 3/2011 | Steinberg | 2012/0004791 A1 | 1/2012 | Buelthoff |
| 2011/0074675 A1 | 3/2011 | Shiming | 2012/0007839 A1 | 1/2012 | Tsao et al. |
| 2011/0081000 A1 | 4/2011 | Gertner | 2012/0019645 A1 | 1/2012 | Maltz |
| 2011/0081043 A1 | 4/2011 | Sabol | 2012/0020524 A1 | 1/2012 | Ishikawa |
| 2011/0085704 A1 | 4/2011 | Han | 2012/0021806 A1 | 1/2012 | Naltz |
| 2011/0092781 A1 | 4/2011 | Gertner | 2012/0027226 A1 | 2/2012 | Desenberg |
| 2011/0102549 A1 | 5/2011 | Takahashi | 2012/0029345 A1 | 2/2012 | Mahfouz et al. |
| 2011/0105883 A1 | 5/2011 | Lake et al. | 2012/0032882 A1 | 2/2012 | Schlachta |
| 2011/0105893 A1 | 5/2011 | Akins | 2012/0033083 A1 | 2/2012 | Horvinger |
| 2011/0115793 A1 | 5/2011 | Grycewicz | 2012/0035462 A1 | 2/2012 | Maurer, Jr. et al. |
| 2011/0115892 A1 | 5/2011 | Fan | 2012/0039505 A1 | 2/2012 | Vastide |
| 2011/0116683 A1 | 5/2011 | Kramer et al. | 2012/0044363 A1 | 2/2012 | Lu |
| 2011/0117528 A1 | 5/2011 | Marciello et al. | 2012/0045091 A1 | 2/2012 | Kaganovich |
| 2011/0118032 A1 | 5/2011 | Zalewski | 2012/0049453 A1 | 3/2012 | Morichau-Beauchant |
| 2011/0133917 A1 | 6/2011 | Zeng | 2012/0051588 A1 | 3/2012 | McEldowney |
| 2011/0142411 A1 | 6/2011 | Camp | 2012/0051664 A1 | 3/2012 | Gopalakrishnan et al. |
| 2011/0150271 A1 | 6/2011 | Lee | 2012/0052949 A1 | 3/2012 | Weitzner |
| 2011/0157168 A1 | 6/2011 | Bennett | 2012/0056982 A1 | 3/2012 | Katz |
| 2011/0157358 A1 | 6/2011 | Bell | 2012/0057640 A1 | 3/2012 | Shi |
| 2011/0157370 A1 | 6/2011 | Livesey | 2012/0065492 A1 | 3/2012 | Gertner et al. |
| 2011/0160569 A1 | 6/2011 | Cohen et al. | 2012/0065494 A1 | 3/2012 | Gertner et al. |
| 2011/0172060 A1 | 7/2011 | Morales | 2012/0072041 A1 | 3/2012 | Miller |

| | | |
|---|---|---|
| 2012/0075166 A1 | 3/2012 | Marti |
| 2012/0075177 A1 | 3/2012 | Jacobsen |
| 2012/0076369 A1 | 3/2012 | Abramovich |
| 2012/0081504 A1 | 4/2012 | Ng |
| 2012/0083314 A1 | 4/2012 | Ng |
| 2012/0083960 A1 | 4/2012 | Zhu |
| 2012/0086778 A1 | 4/2012 | Lee |
| 2012/0086809 A1 | 4/2012 | Lee |
| 2012/0092445 A1 | 4/2012 | McDowell |
| 2012/0092502 A1 | 4/2012 | Knasel |
| 2012/0093481 A1 | 4/2012 | McDowell |
| 2012/0098938 A1 | 4/2012 | Jin |
| 2012/0101388 A1 | 4/2012 | Tripathi |
| 2012/0105573 A1 | 5/2012 | Apostolopoulos |
| 2012/0106814 A1 | 5/2012 | Gleason et al. |
| 2012/0108909 A1 | 5/2012 | Soobounob |
| 2012/0113140 A1 | 5/2012 | Hilliges |
| 2012/0113223 A1 | 5/2012 | Hilliges |
| 2012/0116202 A1 | 5/2012 | Bangera |
| 2012/0119999 A1 | 5/2012 | Harris |
| 2012/0120072 A1 | 5/2012 | Se |
| 2012/0120237 A1 | 5/2012 | Trepess |
| 2012/0120243 A1 | 5/2012 | Chien |
| 2012/0120277 A1 | 5/2012 | Tsai |
| 2012/0121124 A1 | 5/2012 | Bammer |
| 2012/0124604 A1 | 5/2012 | Small |
| 2012/0127319 A1 | 5/2012 | Rao |
| 2012/0133616 A1 | 5/2012 | Nishihara |
| 2012/0133889 A1 | 5/2012 | Bergt |
| 2012/0143029 A1 | 6/2012 | Silverstein |
| 2012/0143212 A1 | 6/2012 | Madhani |
| 2012/0154272 A1 | 6/2012 | Hildreth |
| 2012/0154511 A1 | 6/2012 | Hsu |
| 2012/0154536 A1 | 6/2012 | Stoker |
| 2012/0154579 A1 | 6/2012 | Hanpapur |
| 2012/0156661 A1 | 6/2012 | Smith |
| 2012/0158197 A1 | 6/2012 | Hinman |
| 2012/0162378 A1 | 6/2012 | El Dokor |
| 2012/0165964 A1 | 6/2012 | Flaks |
| 2012/0167143 A1 | 6/2012 | Longet |
| 2012/0169841 A1 | 7/2012 | Chemali |
| 2012/0176314 A1 | 7/2012 | Jeon |
| 2012/0184371 A1 | 7/2012 | Shum |
| 2012/0188237 A1 | 7/2012 | Han |
| 2012/0188371 A1 | 7/2012 | Chen |
| 2012/0194422 A1 | 8/2012 | El Dokor |
| 2012/0194517 A1 | 8/2012 | Ivadi |
| 2012/0194561 A1 | 8/2012 | Grossinger |
| 2012/0195466 A1 | 8/2012 | Teng |
| 2012/0196660 A1 | 8/2012 | Eo Dokor |
| 2012/0197135 A1 | 8/2012 | Slatkine |
| 2012/0200676 A1 | 8/2012 | Huitema |
| 2012/0201428 A1 | 8/2012 | Joshi et al. |
| 2012/0206604 A1 | 8/2012 | Jones |
| 2012/0212594 A1 | 8/2012 | Barns |
| 2012/0218407 A1 | 8/2012 | Chien |
| 2012/0218421 A1 | 8/2012 | Chien |
| 2012/0220233 A1 | 8/2012 | Teague |
| 2012/0224666 A1 | 9/2012 | Speller |
| 2012/0224743 A1 | 9/2012 | Rodriguez |
| 2012/0225718 A1 | 9/2012 | Zhang |
| 2012/0229643 A1 | 9/2012 | Chidanand |
| 2012/0229651 A1 | 9/2012 | Takizawa |
| 2012/0230561 A1 | 9/2012 | Qureshi |
| 2012/0235896 A1 | 9/2012 | Jacobsen |
| 2012/0238337 A1 | 9/2012 | French |
| 2012/0242816 A1 | 9/2012 | Cruz |
| 2012/0249741 A1 | 10/2012 | Maciocci |
| 2012/0253201 A1 | 10/2012 | Reinhold |
| 2012/0253241 A1 | 10/2012 | Ludital |
| 2012/0262540 A1 | 10/2012 | Rondinelli |
| 2012/0262558 A1 | 10/2012 | Boger |
| 2012/0262583 A1 | 10/2012 | Bernal |
| 2012/0275649 A1 | 11/2012 | Cobb |
| 2012/0276995 A1 | 11/2012 | Lansdale |
| 2012/0277001 A1 | 11/2012 | Lansdale |
| 2012/0281093 A1 | 11/2012 | Fong |
| 2012/0281873 A1 | 11/2012 | Brown |
| 2012/0288142 A1 | 11/2012 | Gossweiler, III |
| 2012/0288143 A1 | 11/2012 | Ernst |
| 2012/0288852 A1 | 11/2012 | Willson |
| 2012/0289334 A9 | 11/2012 | Mikhailov |
| 2012/0289822 A1 | 11/2012 | Shachar et al. |
| 2012/0293412 A1 | 11/2012 | El Dokor |
| 2012/0293506 A1 | 11/2012 | Vertucci |
| 2012/0293663 A1 | 11/2012 | Liu |
| 2012/0294511 A1 | 11/2012 | Datta |
| 2012/0300961 A1 | 11/2012 | Moeller |
| 2012/0303839 A1 | 11/2012 | Jackson |
| 2012/0304126 A1 | 11/2012 | Lavigne |
| 2012/0307075 A1 | 12/2012 | Nargalit |
| 2012/0307207 A1 | 12/2012 | Abraham |
| 2012/0314066 A1 | 12/2012 | Lee |
| 2012/0315016 A1 | 12/2012 | Fung |
| 2012/0319946 A1 | 12/2012 | El Dokor |
| 2012/0319989 A1 | 12/2012 | Argiro |
| 2012/0320178 A1 | 12/2012 | Siegert et al. |
| 2012/0320219 A1 | 12/2012 | David |
| 2012/0326966 A1 | 12/2012 | Rauber |
| 2012/0326979 A1 | 12/2012 | Geisert |
| 2012/0327241 A1 | 12/2012 | Howe |
| 2012/0327246 A1 | 12/2012 | William, Sr. |
| 2013/0002866 A1 | 1/2013 | Hanpapur |
| 2013/0002879 A1 | 1/2013 | Weber |
| 2013/0002900 A1 | 1/2013 | Gossweiler, III |
| 2013/0009865 A1 | 1/2013 | Valik |
| 2013/0010071 A1 | 1/2013 | Valik |
| 2013/0013452 A1 | 1/2013 | Dennard |
| 2013/0016009 A1 | 1/2013 | Godfrey |
| 2013/0016876 A1 | 1/2013 | Wooley |
| 2013/0021434 A1 | 1/2013 | Ahiska |
| 2013/0021578 A1 | 1/2013 | Chen |
| 2013/0024819 A1 | 1/2013 | Rieffel |
| 2013/0030283 A1 | 1/2013 | Vortman et al. |
| 2013/0033640 A1 | 2/2013 | Lee |
| 2013/0033700 A1 | 2/2013 | Hallil |
| 2013/0035590 A1 | 2/2013 | Ma et al. |
| 2013/0035612 A1 | 2/2013 | Mason |
| 2013/0040720 A1 | 2/2013 | Cammegh |
| 2013/0041368 A1 | 2/2013 | Cunninghan |
| 2013/0049756 A1 | 2/2013 | Ernst et al. |
| 2013/0057702 A1 | 3/2013 | Chavan |
| 2013/0064426 A1 | 3/2013 | Watkins, Jr. |
| 2013/0064427 A1 | 3/2013 | Picard |
| 2013/0065517 A1 | 3/2013 | Svensson |
| 2013/0066448 A1 | 3/2013 | Alonso |
| 2013/0066526 A1 | 3/2013 | Mondragon |
| 2013/0069773 A1 | 3/2013 | Li |
| 2013/0070201 A1 | 3/2013 | Shahidi |
| 2013/0070257 A1 | 3/2013 | Wong |
| 2013/0072787 A1 | 3/2013 | Wallace et al. |
| 2013/0076863 A1 | 3/2013 | Rappel |
| 2013/0076944 A1 | 3/2013 | Kosaka |
| 2013/0077823 A1 | 3/2013 | Mestha |
| 2013/0079033 A1 | 3/2013 | Gupta |
| 2013/0084980 A1 | 4/2013 | Hammontree |
| 2013/0088584 A1 | 4/2013 | Malhas |
| 2013/0093866 A1 | 4/2013 | Ohlhues et al. |
| 2013/0096439 A1 | 4/2013 | Lee |
| 2013/0108979 A1 | 5/2013 | Daon |
| 2013/0113791 A1 | 5/2013 | Isaacs et al. |
| 2013/0211421 A1 | 8/2013 | Abovitz et al. |
| 2014/0037174 A1 | 2/2014 | Ernst et al. |
| 2014/0073908 A1 | 3/2014 | Biber |
| 2014/0159721 A1 | 6/2014 | Grodzki |
| 2014/0205140 A1 | 7/2014 | Lovberg et al. |

FOREIGN PATENT DOCUMENTS

| | | |
|---|---|---|
| EP | 1524626 A2 | 4/2005 |
| EP | 2515139 | 10/2012 |
| WO | WO 96/17258 A2 | 6/1996 |
| WO | WO 00/72039 A1 | 11/2000 |
| WO | WO 03/003796 A1 | 1/2003 |
| WO | WO 2004/023783 A2 | 3/2004 |
| WO | WO 2007/136745 | 11/2007 |
| WO | WO 2009/129457 A1 | 10/2009 |
| WO | WO 2011/113441 A2 | 9/2011 |

| | | | |
|---|---|---|---|
| WO | WO 2012/046202 A1 | 4/2012 | |
| WO | WO 2013/032933 A2 | 3/2013 | |
| WO | WO 2014/116868 | 7/2014 | |
| WO | WO 2014/120734 | 8/2014 | |

OTHER PUBLICATIONS

Aksoy et al., "Hybrind Prospective and Retrospective Head Motion Correction to Mitigate Cross-Calibration Errors", NIH Publication, Nov. 2012.

Aksoy et al., "Real-Time Optical Motion Correction for Diffusion Tensor Imaging, Magnetic Resonance in Medicine" (Mar. 22, 2011) 66 366-378.

Andrews et al., "Prospective Motion Correction for Magnetic Resonance Spectroscopy Using Single Camera Retro-Grate Reflector Optical Tracking, Journal of Magnetic Resonance Imaging" (Feb. 2011) 33(2): 498-504.

Angeles, Jorge, et al., "The Online Solution of the Hand-Eye Problem", IEEE Transactions on Robotics and Automation, 16(6): 720-731 (Dec. 2000).

Bandettini, Peter A., et al., "Processing Strategies for Time-Course Data Sets in Functional MRI of the Human Breain", Magnetic Resonance in Medicine 30: 161-173 (1993).

Barmet et al, Spatiotemporal Magnetic Field Monitoring for MR, Magnetic Resonance in Medicine (Feb. 1, 2008) 60: 187-197.

Bartels, LW, et al., "Endovascular interventional magnetic resonance imaging", Physics in Medicine and Biology 48: R37-R64 (2003).

Carranza-Herrezuelo et al, "Motion estimation of tagged cardiac magnetric resonance images using variational techniques" Elsevier, Computerized Medical Imaging and Graphics 34 (2010), pp. 514-522.

Chou, Jack C. K., et al., "Finding the Position and Orientation of a Sensor on a Robot Manipulator Using Quaternions", The International Journal of Robotics Research, 10(3): 240-254 (Jun. 1991).

Cofaru et al "Improved Newton-Raphson digital image correlation method for full-field displacement and strain calculation," Department of Materials Science and Engineering, Ghent University St-Pietersnieuwstraat, Nov. 20, 2010.

Ernst et al., "A Novel Phase and Frequency Navigator for Proton Magnetic Resonance Spectroscopy Using Water-Suppression Cycling, Magnetic Resonance in Medicine" (Jan. 2011) 65(1): 13-7.

Eviatar et al., "Real time head motion correction for functional MRI", In: Proceedings of the International Society for Magnetic Resonance in Medicine (1999) 269.

Forbes, Kristen P. N., et al., "Propeller MRI: Clinical Testing of a Novel Technique for Quantification and Compensation of Head Motion", Journal of Magnetic Resonance Imaging 14: 215-222 (2001).

Glover, Gary H., et al., "Self-Navigated Spiral fMRI: Interleaved versus Single-shot", Magnetic Resonance in Medicine 39: 361-368 (1998).

Gumus et al., "Elimination of DWI signal dropouts using blipped gradients for dynamic restoration of gradient moment", ISMRM 20th Annual Meeting & Exhibition, May 7, 2012.

Herbst et al., "Preventing Signal Dropouts in DWI Using Continous Prospective Motion Correction", Proc. Intl. Soc. Mag. Reson. Med. 19 (May 2011) 170.

Herbst et al., "Prospective Motion Correction With Continuous Gradient Updates in Diffusion Weighted Imaging, Magnetic Resonance in Medicine" (2012) 67:326-338.

Horn, Berthold K. P., "Closed-form solution of absolute orientation using unit quaternions", Journal of the Optical Society of America, vol. 4, p. 629-642 (Apr. 1987).

International Preliminary Report on Patentability for Application No. PCT/US2007/011899, dated Jun. 8, 2008, in 13 pages.

International Search Report and Written Opinion for Application No. PCT/US2007/011899, dated Nov. 14, 2007.

International Search Report and Written Opinion for Application No. PCT/US2014/013546, dated May 26, 2014, in 14 pages.

International Search Report and Written Opinion for Application No. PCT/US2014/012806, dated May 15, 2014, in 17 pages.

International Search Report and Written Opinion for Application No. PCT/US2012/052349, dated Feb. 28, 2013, in 16 pages.

Josefsson et al. "A flexible high-precision video system for digital recording of motor acts through lightweight reflect markers", Computer Methods and Programs in Biomedicine, vol. 49:111-129 (1996).

Kiruluta, Andrew, et al., "Predictive Head Movement Tracking Using a Kalman Filter", IEEE Trans. On Systems, Man, and Cybernetics-Part B: Cybernetics, 27(2):326-331 (Apr. 1997).

Maclaren et al., "Combined Prospective and Retrospective Motion Correction to Relax Navigator Requirements", Magnetic Resonance in Medicine (Feb. 11, 2011) 65:1724-1732.

MacLaren et al., "Navigator Accuracy Requirements for Prospective Motion Correction", Magnetic Resonance in Medicine (Jan. 2010) 63(1): 162-70.

MacLaren, "Prospective Motion Correction in MRI Using Optical Tracking Tape", Book of Abstracts, ESMRMB (2009).

McVeigh, Elliot R. et al., "Real-time, Interactive MRI for Cardiovascular Interventions", Academic Radiology, 12(9): 1121-1127 (2005).

Nehrke et al., "Prospective Correction of Affine Motion for Arbitrary MR Sequences on a Clinical Scanner", Magnetic Resonance in Medicine (Jun. 28, 2005) 54:1130-1138.

Norris et al., "Online motion correction for diffusion-weighted imaging using navigator echoes: application to RARE imaging without sensitivity loss", Magnetic Resonance in Medicine, vol. 45:729-733 (2001).

Ooi et al., "Prospective Real-Time Correction for Arbitrary Head Motion Using Active Markers", Magnetic Resonance in Medicine (Apr. 15, 2009) 62(4): 943-54.

Orchard et al., "MRI Reconstruction using real-time motion tracking: A simulation study", Signals, Systems and Computers, 42nd Annual Conference IEEE, Piscataway, NJ, USA (Oct. 26, 2008).

Park, Frank C. and Martin, Bryan J., "Robot Sensor Calibration: Solving AX=XB on the Euclidean Group", IEEE Transaction on Robotics and Automation, 10(5): 717-721 (Oct. 1994).

Qin et al., "Prospective Head-Movement Correction for High-Resolution MRI Using an In-Bore Optical Tracking System", Magnetic Resonance in Medicine (Apr. 13, 2009) 62: 924-934.

Schulz et al., "First Embedded In-Bore System for Fast Optical Prospective Head Motion-Correction in MRI", Proceedings of the 28th Annual Scientific Meeting of the ESMRMB (Oct. 8, 2011) 369.

Shiu, Yiu Cheung, and Ahmad, Shaheen, "Calibration of Wrist-Mounted Robotic Sensors by Solving Homogeneous Transform Equations of the Form AX=XB", IEEE Transactions on Robotics and Automation, 5(1): 16-29 (Feb. 1989).

Tremblay, Marleine, et al., "Retrospective Coregistration of Functional Magnetic Resonance Imaging Data using External monitoring", Magnetic Resonance in Medicine 53:141-149 (2005).

Tsai, Roger Y. and Lenz, Reimer K., "A New Technique for Fully Autonomous and Efficient 3D Robotics Hand/Eye Calibration", IEEE Transaction on Robotics and Automation, 5(3): 345-358 (Jun. 1989).

Wang, Ching-Cheng, "Extrinsic Calibration of a Vision Sensor Mounted on a Robot", IEEE Transactions on Robotics and Automation, 8(2):161-175 (Apr. 1992).

Ward, Heidi A., et al., "Prospective Multiaxial Motion Correction for fMRI", Magnetic Resonance in Medicine 43:459-469 (2000).

Welch, Edward Brian, at al., "Spherical Navigator Echoes for Full 3D Rigid Body Motion Measurement in MRI", Magnetic Resonance in Medicine 47:32-41 (2002).

Zaitsev, M., et al., "Prospective Real-Time Slice-by-Slice 3D Motion Correction for EPI Using an External Optical Motion Tracking System", Proc.Intl.Soc.Mag.Reson.Med.11:517(2004).

Zeitsev et al., "Magnetic resonance imaging of freely moving objects: Prospective real-time motion correction using an external optical motion tracking system", NeuroImage 31 (Jan. 29, 2006) 1038-1050.

Maclaren et al., "Measurement and correction of microscopic head motion during magnetic resonance imaging of the brain", PLOS ONE, vol. 7(11):1-9 (2012).

\* cited by examiner

*Primary Examiner* — Manav Seth

(74) *Attorney, Agent, or Firm* — Knobbe Martens Olson & Bear LLP

(57) ABSTRACT

This invention relates to a system that adaptively compensates for subject motion in real-time in an imaging system. An object orientation marker (30), preferably a retro-grate reflector (RGR), is placed on the head or other body organ of interest of a patient (P) during a scan, such as an MRI scan. The marker (30) makes it possible to measure the six degrees of freedom (x, y, and z-translations, and pitch, yaw, and roll), or "pose", required to track motion of the organ of interest. A detector, preferably a camera (40), observes the marker (30) and continuously extracts its pose. The pose from the camera (40) is sent to the scanner (120) via an RGR processing computer (50) and a scanner control and processing computer (100), allowing for continuous correction of scan planes and position (in real-time) for motion of the patient (P). This invention also provides for internal calibration and for co-registration over time of the scanner's and tracking system's reference frames to compensate for drift and other inaccuracies that may arise over time.

31 Claims, 13 Drawing Sheets

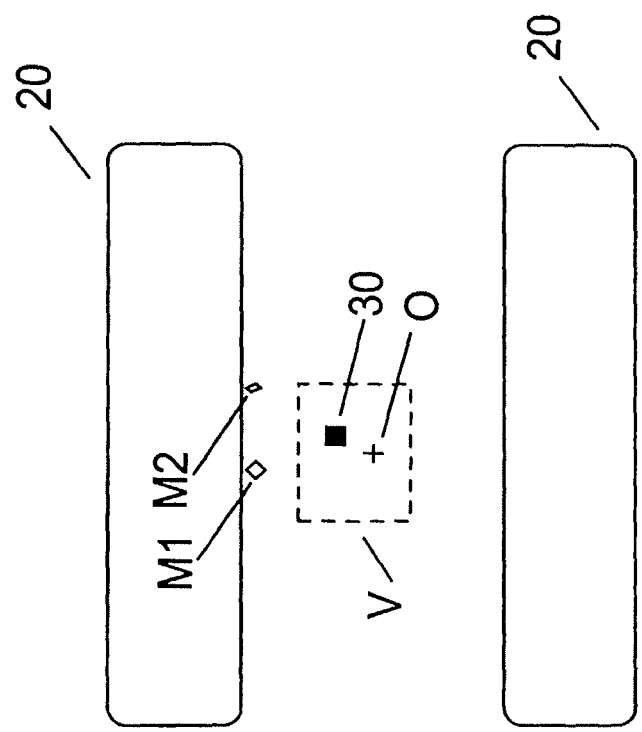
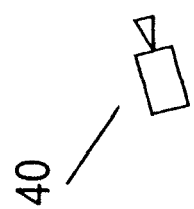
Fig. 6

US 9,138,175 B2

MOTION TRACKING SYSTEM FOR REAL TIME ADAPTIVE IMAGING AND SPECTROSCOPY

CROSS-REFERENCE TO RELATED APPLICATIONS

This application is a continuation of U.S. patent application Ser. No. 14/034,252, titled MOTION TRACKING SYSTEM FOR REAL TIME ADAPTIVE IMAGING AND SPECTROSCOPY and filed Sep. 23, 2013, which is a continuation of U.S. patent application Ser. No. 13/735,907, titled MOTION TRACKING SYSTEM FOR REAL TIME ADAPTIVE IMAGING AND SPECTROSCOPY and filed Jan. 7, 2013, which is a continuation of U.S. patent application Ser. No. 13/338,166, titled MOTION TRACKING SYSTEM FOR REAL TIME ADAPTIVE IMAGING AND SPECTROSCOPY and filed Dec. 27, 2011, and now U.S. Pat. No. 8,374,411, which is a continuation of U.S. patent application Ser. No. 11/804,417, titled MOTION TRACKING SYSTEM FOR REAL TIME ADAPTIVE IMAGING AND SPECTROSCOPY and filed May 18, 2007, and now U.S. Pat. No. 8,121,361, which claims priority to U.S. Provisional Application No. 60/802,216, titled MRI MOTION ACCOMMODATION and filed May 19, 2006. The foregoing applications are hereby incorporated herein by reference in their entirety.

STATEMENT REGARDING FEDERALLY SPONSORED R&D

This invention was made with government support under Grant numbers 5K02 DA016991 and 5ROI DA021146 awarded by the National Institutes of Health. The government has certain rights in the invention.

FIELD

This invention relates generally to the field of medical imaging, and more specifically to a system for correcting defects in medical images that are caused by a patient's movement during long duration in vivo (in the living body) scans, such as magnetic resonance scans.

BACKGROUND

"Tomographic" imaging techniques make images of multiple slices of an object. Multiple tomographic images can then be aligned and assembled using a computer to provide a three dimensional view. Some commonly used tomographic imaging techniques include magnetic resonance imaging (MRI) and magnetic resonance spectroscopy (MRS) techniques, which are ideal for assessing the structure, physiology, chemistry and function of the human brain and other organs, in vivo. Because the object of interest is often imaged in many slices and scanning steps in order to build a complete three dimensional view, scans are of long duration, usually lasting several minutes. To increase resolution (detail) of a tomographic scan, more slices and more scanning steps must be used, which further increases the duration of a scan. Magnetic resonance and other long duration imaging techniques (including tomographic techniques), now know or hereafter invented (hereinafter collectively referred to as "MR" or "MRI") can also afford relatively high spatial and temporal resolution, are non-invasive and repeatable, and may be performed in children and infants.

In addition to MR, other types of scans require multiple repeated exposures, separated in time, of an entire (not slices) object (such as an organ), such as angiograms, in which a dye is injected into a blood vessel and then scans separated in time are taken to determine how and where the dye spreads. These types of scans that detect motion inside a patient or other object over time ("digital angiography systems") can also have a long duration, and be subject to the problem of patient or object motion.

Many tomographic imaging techniques rely on detecting very small percentage changes in a particular type of signal, which makes these techniques even more susceptible to movements. In functional magnetic resonance imaging, for example, changes in the properties of blood in brain areas activated while subjects are performing tasks causes small signal changes (on the order of a few percent) that can be detected with MR. However, these small signal changes may easily be obscured by signal changes of similar or even greater size that occur during unintentional subject movements.

Because tomographic techniques require that so many images be taken (because so many slices and scanning steps are necessary), the scan has a long duration, so that motion of the subject is a substantial problem for acquiring accurate data. Consequently, subjects commonly are required to lie still to within one millimeter and one degree over extended time periods. Similar requirements exist for other modem imaging techniques, such as Positron Emission Tomography (PET), Single Photon Emission Computerized Tomography (SPECT) and "computer tomography" (CT). These strict requirements cannot be met by many subjects in special populations, such as children and infants, very sick patients, subjects who are agitated perhaps due to anxiety or drug use, or patients with movement disorders, resulting in data with motion artifacts. Similarly, it is exceedingly difficult to perform scans in awake animals.

The basic problem is that it may take several minutes for a scan to be completed, but the patient or other object being scanned cannot remain still for several minutes. Further, the space for a patient or other object being scanned (the "scanning volume") in an MR machine is very limited—there is very little space in an MR machine once a patient has been positioned inside for a scan.

Several techniques have been developed over the past decades to reduce the sensitivity of scans to motion of the patient or other object being scanned.

Early techniques utilized specially designed scan sequences ("first-order flow/motion compensation") to minimize the effects of motion. While these approaches are particularly useful for reducing artifacts (or imaging errors) due to flowing blood, swallowing or eye movements, they afford little improvement during movements of entire organs, such as head movements.

Articles entitled "Self-navigated spiral fMRI: interleaved versus single-shot" by Glover G H, et al, in Magnetic Resonance in Medicine 39: 361-368 (1998), and "PROPELLER MRI: clinical testing of a novel technique for quantification and compensation of head motion" by Forbes K, et al, in the Journal of Magnetic Resonance Imaging 14(3): 215-222 (2001), both incorporated herein by reference, disclose how improved sampling schemes for the MRI data can reduce sensitivity to motion. These techniques can reduce motion sensitivity of MR scans under certain conditions, but cannot eliminate errors from motion under all conditions or for very quick movements.

With certain modern ultra-fast "single-shot" imaging techniques (such as "echoplanar imaging"), the entire head (or other organ of interest) is scanned continuously every few seconds (over the course of minutes), for instance, for "functional MRI". This makes it possible to determine the "pose", defined as position and rotation, of the head at each instant relative to the initial pose, using image registration (alignment of images). Once the pose for a given instant is known (relative to the initial image), the scanner's image for that instant can be re-aligned to the initial image. For example, the article entitled "Processing strategies for time-course data sets in functional MRI of the human brain" by Bandettini P A, et al, in Magnetic Resonance Medicine 30: 161-173 (1993), incorporated herein by reference, disclosed how realignment of MRI volumes (consisting of multiple slices) can be used to correct for head motion in functional MRI time series. However, these methods are inherently slow because they use MRI, i.e. they correct movements only every few seconds, and are unable to correct for motion in certain directions (orthogonal to the scan planes; in other words, towards or away from the planes in which the scans are being taken).

While all of these techniques reduce sensitivity to subject motion, several problems remain. One major problem is related to the manner in which typical tomographic imaging methods acquire data. Specifically, the data for each cross section (slice) is acquired by moving step by step along "lines" in a mathematical space ("k-space"). The data acquisition step is typically repeated hundreds of times, until all lines in the k-space have been filled. For all methods described above, even if motion sensitivity for each individual acquisition (defining a line in k-space) is reduced, these methods typically do not account for variations in head pose amongst the different k-space lines. Second, the methods poorly tolerate fast movements within individual acquisition steps. Finally, one of the most significant issues is that none of these techniques can be applied universally across all the various scanning methods (pulse sequences—the order and manner in which slices are imaged) used in MRI or other tomographic scanning techniques.

One of the most promising approaches to motion correction is to track the pose of the head, brain or other organ of interest (or other object) in real time, during a scan, and to use this pose information to compensate for the detected motion in data acquisitions for subsequent slices within the same scan. This is called adaptive imaging, because the image is adapted during the scan to compensate for the detected motion.

One important aspect of adaptive imaging is the accuracy (or "resolution") of the motion tracking system. Because of the high resolution needed for medical imaging, the motion tracking system must also have a high resolution, because the motion tracking system's information will be used to align the images of each slice. If the motion tracking system's resolution is high enough, each of the scan images can be accurately aligned (registered) despite a patient's motion.

An article entitled "Prospective multi axial motion correction for fMRI" by Ward H A, et al, in Magnetic Resonance in Medicine 43:459-469 (2000), incorporated herein by reference, discloses the use of "navigator" signals to estimate the pose of the head and to dynamically correct for head motion.

An article entitled "Spherical navigator echoes for full 3D rigid body motion measurement in MRI" by Welch E B, et al, in Magnetic Resonance in Medicine 47:32-41 (2002), incorporated herein by reference, discloses the use of an MR-based navigator for adaptive motion correction in MRI.

Similarly, an article entitled "Endovascular interventional magnetic resonance imaging." by Bartels L W, et al, in Physics in Medicine and Biology 48(14): R37-R64 (2003), and another article entitled "Real-time, Interactive MRI for cardiovascular interventions" by McVeigh E R, et al, in Academic Radiology 12(9): 1121-1127 (2005), both of which are incorporated herein by reference, disclose the use of small radio frequency (RF) coils for tracking catheters during interventional MRI.

While these MR-based "adaptive MRI" techniques provide good results in many situations, they intrinsically interfere with MR acquisitions, work only for a limited number of MR sequences, and are limited to measuring the position or pose a few times per second only.

In order to overcome these shortcomings, recent approaches to real time (lion the fly") motion correction utilize optical techniques to track subject motion, rather than MR-based methods. The pose information from the tracking system is sent to the scanner and used by the scanner to compensate for the motion in real time. Optical systems are very suitable among alternative tracking technologies because they provide accurate, non-contact sensing with a passive and non-magnetic target. In particular, stereovision (SV) systems have been used for motion tracking for medical imaging.

Stereovision systems employ a target with 3 or more visible landmarks, and at least 2 tracking cameras. By detecting the landmarks in images captured by the cameras and comparing their measured positions and shapes to the known shape of the target, the target position and orientation can be determined, SV systems offer important features including sub-millimeter accuracy when fully calibrated, and update rates limited only by the camera and computing hardware.

However, SV systems have three limitations for adaptive MR imaging: (1) measurement accuracy decreases as the distance between the cameras becomes smaller, (2) the accuracy of orientation measurement decreases as the target becomes smaller; and (3) SV systems have high sensitivity to errors in internal calibration, i.e. small errors in the relative position or rotation of the cameras may cause large errors in the measured target pose. Therefore, SV systems require periodic recalibration. However, accurate calibration has to be performed manually, using a specialized calibration tool or target, is time consuming, and cannot be done while patients are being scanned.

Furthermore, stereovision systems achieve their best accuracy when the separation distance between the cameras is comparable to the distance between the cameras and the target. However, this ideal separation is not possible in an MR scanner because the opening to the scanning volume (the volume which can be scanned by the scanner) is relatively narrow, making it impossible to move the cameras sufficiently far apart and still view into the scanning volume. Additionally, tracking with SV cameras works optimally with larger tracking targets; however, the space in the MR or other scanner environment is very limited.

As noted above, slight errors in the internal calibration of SV systems can produce large measurement errors. For example, an article entitled "Prospective Real-Time Slice-by-Slice 3D Motion Correction for EPI Using an External Optical Motion Tracking System" by Zaitsev, M C et al, ISMRM 12, Kyoto (2004), which is incorporated herein by reference, tested the use of an SV system for adaptive functional MRI. The system was able to provide 0.4 mm accuracy when ideally calibrated. However, the study contains information showing that a tiny 1I100th degree change in the camera alignments can produce a 2.0 mm error in the position measurement and the study co-authors privately communicated to the present inventors that maintaining calibration was impracticably difficult. Even with extremely careful and rigid engineering of the camera module of an SV system, a measurement drift on the order of 1 mm can be observed while the SV motion tracker warms up, and recommend warm-up periods are 1 to 1.5 hours to avoid drift. Tremblay M, Tam F, Graham S J. Retrospective Coregistration of Functional Magnetic Resonance Imaging Data Using External Monitoring. Magnetic Resonance in Medicine 2005; 53:141-149, incorporated herein by reference.

The prior art has no means to track or correct for these slow changes while the medical imaging system is in service, imaging patients. The error which accumulates in the co-registration, because of loss of camera calibration, is a severe problem for motion compensation in medical imaging using an external tracking system.

As a result, an SV tracking system requires frequent recalibration to accurately determine its position relative to the imaging system. The recalibration procedure involves scanning a specialized calibration tool or sample ("phantom") at multiple, manually-adjusted positions, both with the Medical imaging system and the SV system.

An article entitled "Closed-form solution of absolute orientation using unit quaternions" by Horn, B K P, J. Opt. Soc. Am. 1987; 4:629-642, which is incorporated herein by reference, describes the commonly used "absolute orientation" method. However, since time on a medical imaging system is limited and expensive, removing patients and conducting repeated recalibration with a specialized calibration tool is prohibitively expensive.

Furthermore, Zaitsev et al utilized a relatively large reflective marker approximately 10 em (4 inches) in size, which was affixed to the subjects' head in the scanner by means of a bite bar. While a bite bar may be tolerated by healthy and cooperative volunteers, it is an impractical solution for sick or demented patients, or young children.

Therefore, while stereovision systems are able to track subject motion for use with adaptive imaging techniques when conditions are ideal, the use of SV systems for routine clinical scans proves impractical due to cumbersome recalibration procedures, instabilities over time, and awkward size and attachment of tracking markers (i.e. large marker requiring use of a bite bar).

Motion tracking can be improved using prediction means to predict motion, including (without limitation) motion filter and prediction methods. For adaptive MR imaging, the scanner controller requires values of the subject pose at the exact instant adjustments to the scan are applied (Scanning Timing Information), The determination of the subject pose based on actual measurements is an estimation problem. The simplest estimator takes the most recent measurement as the current pose. This simple estimator has been used frequently, for example in an article entitled "Prospective Real-Time Slice-by-Slice 3D Motion Correction for EPI Using an External Optical Motion Tracking System" by Zaitsev, M. C., et al, ISMRM 12, Kyoto (2004), incorporated herein by reference.

However, this simple estimator neglects three types of information that can improve the accuracy of the estimate of subject pose: (1) measurements prior to the most recent measurement may add information (reduce the covariance of the estimate) if those prior measurements disclose a velocity of the subject's motion; (2) a biomechanical model, in conjunction with the measurement statistics, can be used to constrain the estimated motion (the subject's body only moves in certain ways); and (3) information about the lag time between the pose measurement and the time of the MR scans. By utilizing these additional sources of information, the accuracy of motion tracking and thus of adaptive imaging will be enhanced.

Extended Kalman filtering, which is essentially model-based filtering with simultaneous estimation of the signals and their statistics, is statistically optimal in certain cases and is the most effective framework for incorporating information of types (1), (2) and (3). Kalman filtering has a long history of use in aerospace applications, such as target tracking, aircraft guidance and formation flying of spacecraft, for example in U.S. Pat. No. 5,886,257 "Autonomous Local Vertical Determination Apparatus and Methods for a Ballistic Body," incorporated herein by reference, which teaches the use of Kalman filtering applied to inertial signals. Kalman filtering has also been previously demonstrated for head motion tracking, for example in "Predictive Head Movement Tracking Using a Kalman Filter", IEEE Trans. on Systems, Man, and Cybernetics Part B: Cybernetics 1997; 27:326-331, by Kiruluta A, Eizenman M, and Pasupathy S, incorporated herein by reference. Kalman filtering is also disclosed in US Patent reference.

Of course, persons of ordinary skill in the art are aware that the prediction means can be implemented in hardware, software, or by other means, and that there are equivalent processes and algorithms to perform the prediction function of the motion filtering and prediction means disclosed above.

U.S. Pat. Nos. 5,936,722, 5,936,723 and 6,384,908 by Brian S. R. Armstrong and Karl B. Schmidt, et al, which are incorporated herein by reference, disclose "Retro-Grate Reflectors", or RGRs, which allow accurate and fast position measurements with a single camera and a single, relatively small and light orientation marker. The RGR allows the visual determination of orientation with respect to the six degrees of freedom (the three linear directions of left and right, up and down, and forward and back, plus the three rotational directions of roll (rotation around a horizontal axis that points straight ahead), pitch (rotation around a horizontal axis that points side to side) and yaw (rotation around a vertical axis that points up and down)) by viewing a single marker. Pose (position and rotation) is orientation with respect to the six degrees of freedom. As used herein, an object orientation marker is any marker, such as an RGR marker, from which at least three degrees of freedom can be determined by viewing or otherwise remotely detecting the marker.

SUMMARY

Conceptually, the present invention generally includes a motion tracking system for an object in the scanning volume of a scanner, comprising: an object orientation marker attached to the object; a detector that repeatedly detects poses of the object orientation marker; a motion tracking computer that analyzes the poses of the object orientation marker to determine motion of the object between the repeated detections and to send tracking information to the scanner to dynamically adjust scans to compensate for motion of the object.

More specifically, the invention comprises: an object orientation marker attached to the object; a camera that records repeated images; a mirror in a fixed position with respect to the scanner positioned so that the camera records repeated reflected images of the orientation marker in the mirror; a motion tracking computer that analyzes the repeated reflected images of the object orientation marker to determine motion of the object between the repeated images and to send tracking information to the scanner to dynamically adjust scans to compensate for motion of said object.

Another aspect of the invention is a process for compensating for patient motion in the scanning volume of a scanner that has a motion tracking system, without a specialized calibration tool, even if the motion tracking system is out of alignment with the scanner, comprising: recording the patient motion both in scans of the patient by the scanner and in the motion tracking system, whereby the patient motion is simultaneously recorded in the coordinate frame of the scanner and in the coordinate frame of the motion tracking system; updating the measurement coordinate transformation from the motion tracking system coordinate frame to the scanner coordinate frame to compensate for drift and other calibration inaccuracies; transforming patient motion recorded in the coordinate frame of the motion tracking system into patient motion in the coordinate frame of the scanner using the updated measurement coordinate transformation.

A general embodiment of this invention comprises an object orientation marker attached to an object; a camera that views the object orientation marker directly; a first mirror in a fixed position with respect to the scanner positioned so that the camera can view a reflected image of the object orientation marker in the first mirror, so that the camera simultaneously records repeated direct images and repeated reflected images of the object orientation marker; and a motion tracking computer that analyzes both the repeated direct images and the repeated reflected images of the object orientation marker to determine motion of the object between the repeated images and to send tracking information to the scanner to dynamically adjust scans to compensate for motion of said object; a mirror orientation marker in a fixed position with respect to the first mirror positioned so that the camera can view a direct image of the mirror orientation marker simultaneously with a reflected image in the first mirror of the object orientation marker; a motion tracking computer that analyzes repeated reflected images of the object orientation marker in the first mirror and repeated direct repeated images of the mirror orientation marker to determine motion of the object between the repeated images and to send tracking information to the scanner to dynamically adjust scans to compensate for motion of said object.

Still another preferred embodiment of the invention comprises: a camera that records repeated images; an object orientation marker attached to the object; a first mirror in a fixed position with respect to the scanner positioned so that the camera can view the object orientation marker in the first mirror; a second mirror in a fixed position with respect to the first mirror positioned so that the camera can view reflected images of the object orientation marker in the second mirror simultaneously with reflected images of the object orientation marker in the first mirror; a mirror orientation marker in a fixed position with respect to the first mirror positioned so that the camera can view direct images of the mirror orientation marker simultaneously with reflected images of the object orientation marker in both the first mirror and the second mirror; a motion tracking computer that analyzes repeated reflected images of the object in the second mirror and repeated direct images of the mirror orientation marker, to determine motion of the object between the repeated images and to send tracking information to the scanner to dynamically adjust scans to compensate for motion of said object.

An additional feature of the present invention is that the mirrors and camera can be internally calibrated by analyzing the repeated direct images and the repeated reflected images.

Optionally, patient motion can be recorded both by scans of the object by the scanner and by repeated images of the object orientation marker, so that such patient motion is recorded in coordinate frames of both the scanner and of the detector and mirrors, whereby patient motion recorded in the coordinate frame of the detector and mirrors can be transformed into patient motion in the coordinate frame of the scanner.

An additional optional feature of the invention includes prediction means to predict orientation of the object at times when scans will be taken by the scanner, including motion filtering and prediction.

Of course, the scanner can be selected from the group consisting of MR scanners, PET scanners, SPECT scanners, CT scanners and digital angiography systems.

Operably the object orientation marker indicates pose in at least 3 degrees of freedom, but preferably the object orientation marker indicates pose in 5 degrees of freedom, and optimally in 6 degrees of freedom.

Preferably, the object orientation marker is an RGR. In general terms, the invention comprises: an adaptive imaging system; a motion tracking system; and a motion filtering and prediction system; wherein the motion tracking system provides tracking information to the adaptive imaging system to dynamically adjust scans to compensate for motion of said object; and wherein the motion filtering and prediction system provides predicted pose of the object when the imaging system takes scans.

Briefly, and in general terms, the present invention provides for a system for automatic real-time correction of subject motion during long duration scans, including (but not limited to) "tomographic" (or cross-sectional) imaging, specifically MRI scans. The present invention is a motion tracking system that is MRI-compatible, highly accurate, robust, self-calibrating, has a potential time resolution in the millisecond range, and can be integrated with any existing MR technique. The adaptive MR system has 3 main components, as shown in FIG. 1: (1) RGR-based tracking system, (2) interface between tracking system and MR scanner, and (3) MR scanner providing scanning sequences that allow dynamic adjustment of geometric scanning parameters (such as slice locations and orientations). The camera-based system relies on Retro-Grate Reflectors, or RGRs, which allow accurate and fast pose measurements with a single camera and a single, relatively small marker (approximately 1 cm size). Pose updates from the tracking system are sent to the MRI scanner via the interface. Tomographic scanning methods make it possible to image multiple cross-sections ("slices") of the body; each slice is defined by a position and rotation in space. The MR scanning sequences continuously read the pose information from the tracking system, and the slice locations and rotations are updated dynamically, such that scanning planes or volumes track the poses of the object (such as an organ) to which the target is attached. This results in scans that are virtually void of motion-artifacts. Very fast movements with velocities of 100 mm/sec or greater can be corrected, which represents an approximate 10 to 100-fold improvement over current techniques.

One important component of the presently preferred embodiment of this invention is the Retro-Grate Reflector (RGR), a new tool that makes it possible to accurately determine the 3 locations and 3 rotations ("6 degrees of freedom" or "pose") of a target from a single image. An RGR target is illustrated in FIG. 13. It is constructed by applying artwork on the front and back of a transparent substrate, such as a glass or plastic plate. The artwork includes a StarBurst landmark, shown in the center of FIG. 13, and circular landmarks. Also included are front and back gratings to produce a series of banded patterns ("moire" patterns), which are shown as light and dark fringes in FIG. 13.

The moire patterns of the RGR target are designed to be exquisitely sensitive to changes in orientation. As a result, the RGR system is able to accurately determine all 6 degrees of freedom (3 translations and 3 rotations) from a single camera image. Of course, an RGR can be used to extract less than 6 degrees of freedom.

In the context of adaptive imaging to correct for subject motion, RGR motion tracking addresses the shortcomings of stereovision by: (1) incorporating only one camera, thus removing the requirement for a significant separation between cameras, and (2) interpreting moire patterns so that high accuracy can be achieved even if the object orientation marker (also referred to as a target or tag) is small, and (3) providing redundant information for use in detecting and correcting drift and other calibration inaccuracies by internal calibration.

If desired, further innovations (described below) allow for 3) simultaneous motion tracking and determination of the internal calibration, 4) use of two or more "visual paths" to avoid loss of sight during large movements, 5) a 10-fold increase in tracking accuracy compared to stereovision, and 6) continuous automatic calibration (or "auto-tuning") of the system in order to eliminate the effect of drift and other calibration inaccuracies, such as those due to temperature changes, vibration, etc.

One innovation is to use a mirror to detect an object orientation marker. A mirror shall include any device to allow an object orientation marker to be viewed along an indirect line of sight, including, without limitation, a prism, a beam splitter, a half silvered mirror, fiber optics, and a small camera.

Another innovation is to incorporate motion filtering and prediction to improve performance of a limited-quality motion sensing means. Motion filtering refers to using information about an object's prior positions to infer its motion and thereby improve accuracy in determining pose (over methods which look only at the most recent position and ignore prior positions).

BRIEF DESCRIPTION OF THE DRAWINGS

FIG. 6 is a side elevational view of the physical layout of a preferred embodiment of adaptive RGR-MRI configuration.

DETAILED DESCRIPTION

Figure 1:
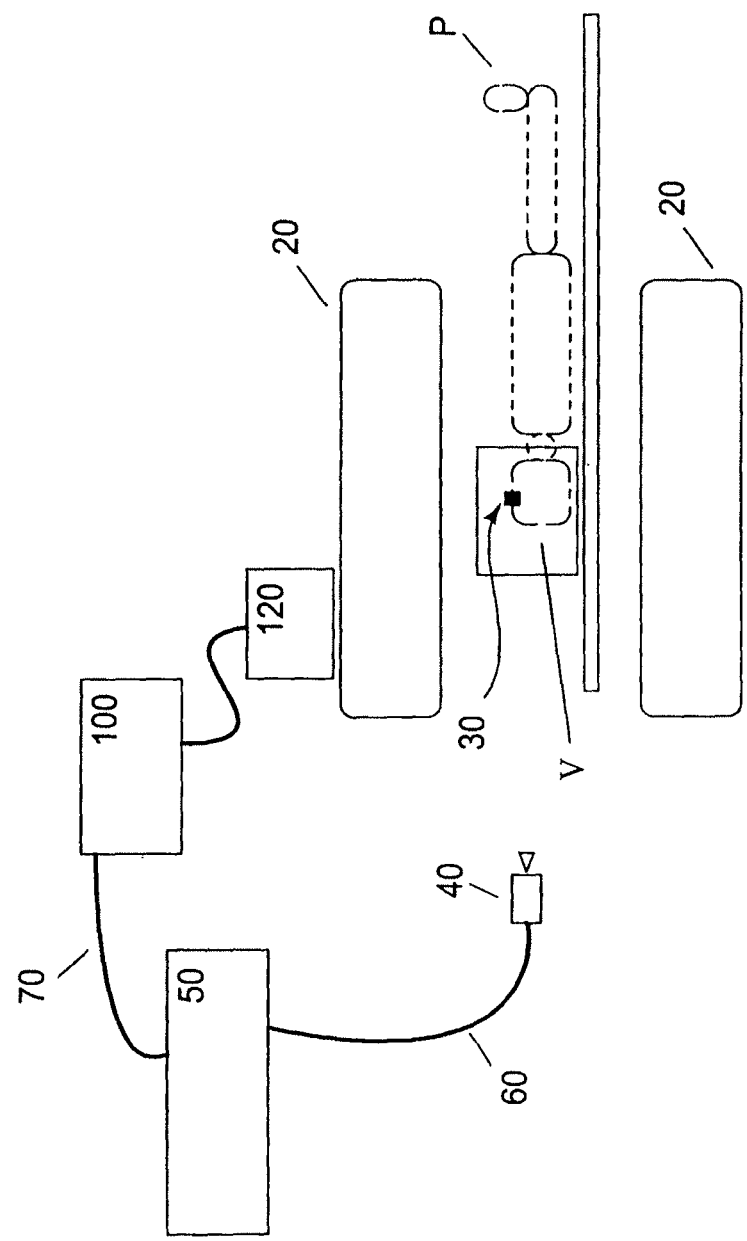
FIG. 1 is a conceptual side elevational view of a system for RGR-based motion tracking for real-time adaptive MR imaging and spectroscopy.
Figure 2:
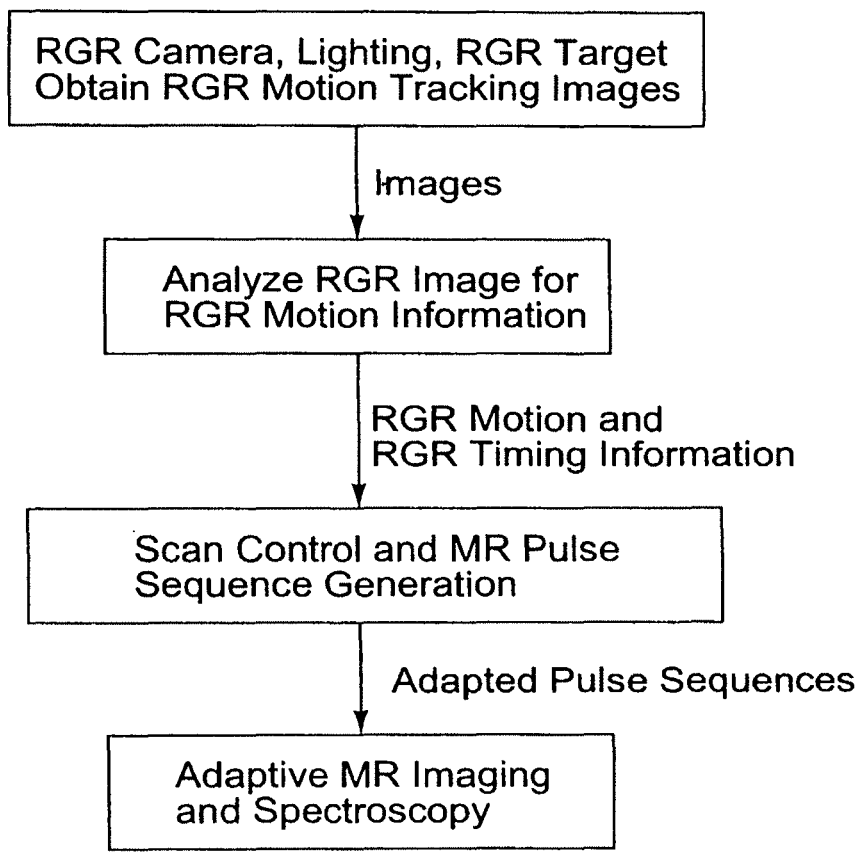
FIG. 2 is a flow chart of steps for adaptive MR imaging in an alternative embodiment, incorporating RGR-based motion sensing for adaptive MR imaging.

FIGS. 1 and 2 illustrate the essential elements of the presently preferred embodiments of a system for motion tracking for real-time adaptive imaging and spectroscopy. The best modes are illustrated by way of example using a patient in an MR scanner and RGR object orientation marker, but of course, other objects can be scanned besides patients, other scanners can be used besides MR scanners, and other object orientation markers can be used besides RGRs.

As shown in FIG. 1, a patient P is imaged in a scanning volume V inside an MR scanner magnet 20. An RGR tag or target 30 is affixed to the patient P near the organ of interest being scanned (e.g., the head). A detector, such as a camera 40 (the "RGR Camera") outside the scanner magnet 20 observes the RGR target 30, either directly or optionally via one or more mirrors on the wall of the scanner bore or in some other convenient location (not shown). As also shown in FIG. 2, the RGR Camera 40 is connected to the RGR Processing Computer 50. The RGR Processing Computer 50 performs several functions, including analyzing images 60 of the RGR to produce RGR Motion Information. Additionally, an accurate clock in the RGR Processing Computer 50 produces Timing Information related to the RGR Motion Information to provide Motion and Timing Information 70.

A Scanner Control and Processing Computer 100 is connected to the MR Scanner 120 and also to the RGR Processing Computer 50. RGR Motion and Timing Information 70 is passed from the RGR Processing Computer 50 to the Scanner Control and Processing Computer 100. In one embodiment, Timing Information related to the MR scan (Scanner Timing Information) is produced by the Scanner Control and Processing Computer 100 and passed to the RGR Processing Computer 50 with a request for RGR Motion Information. The RGR Processing Computer 50 uses the Scanner Timing Information in conjunction with the RGR Motion Information and RGR Timing Information to produce Motion Information at time instants determined by the Scanner Control and Processing Computer 100. Both the scanner and the motion tracking system have inherent lag times between acquiring an image and completing the image, due to computation delays and other factors. The motion tracking system's lag time in acquiring images may be on the order of milliseconds, but the scanner's lag time in acquiring images may be on the order of seconds to minutes.

The Scanner Control and Processing Computer 100 utilizes RGR Motion Information from the RGR Processing Computer 50 and makes calculations to adapt the MR Pulse Sequence (the sequence of pulses used to acquire tomographic images) to the motion information. The adapted MR Pulse Sequence parameters are used to drive the MR Scanner 120.

Figure 3:
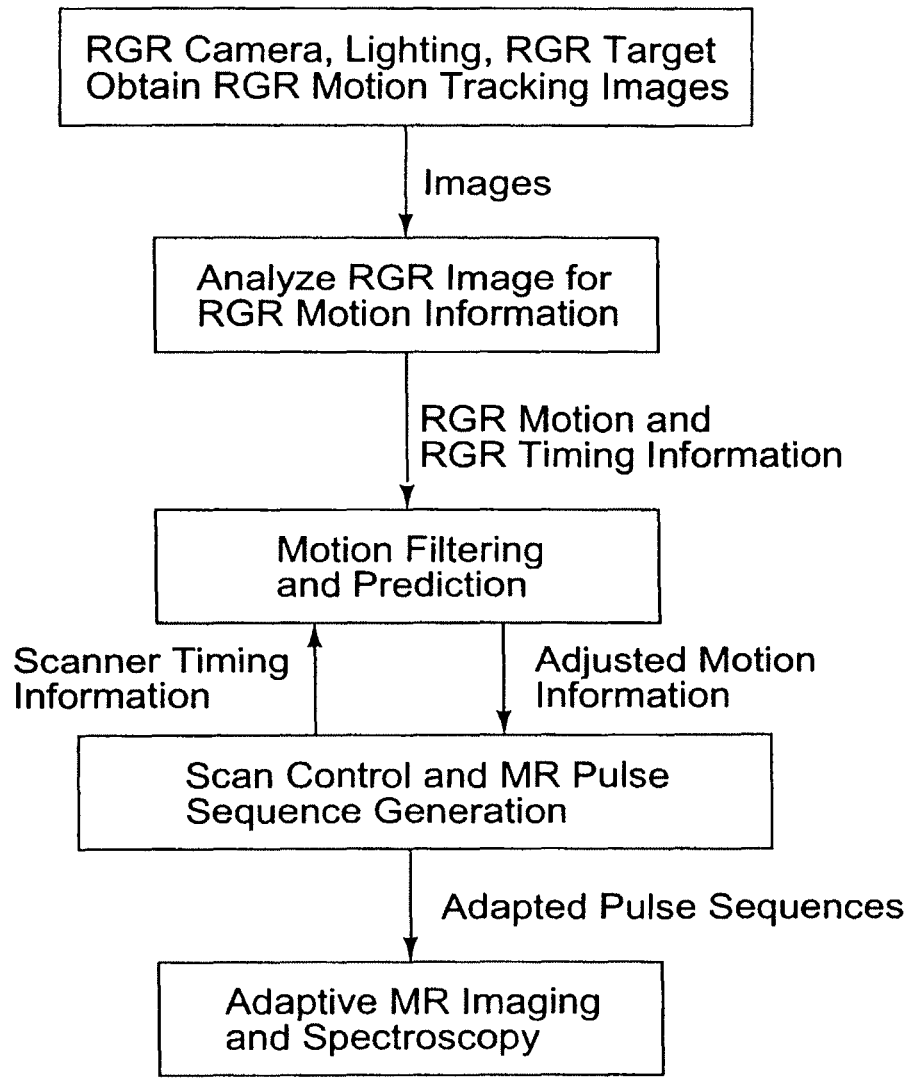
FIG. 3 is a flow chart of steps for RGR-based adaptive MR imaging in the preferred embodiment, incorporating RGR-based adaptive MR imaging and optional motion filtering and prediction.

FIG. 3 provides a flow chart of the steps of the preferred embodiment of RGR based adaptive MR imaging and spectroscopy using optional motion filtering and prediction. System elements of RGR Camera, RGR Lighting and RGR target are used to obtain RGR Motion Tracking Images. The RGR Images are passed to the RGR Processing Computer where they are analyzed, which produces RGR Motion and RGR Timing Information. This information is optionally passed to a Motion Filtering and Prediction routine, which also receives Scanner Timing Information in the form of time values for future instants at which the Scanner Control and Processing Computer will apply Motion Information, The Motion Filtering and Prediction element analyzes a plurality of recent RGR Motion and Timing Information as well as Scanner Timing information to produce Adjusted Motion Information, which is the best estimate of the subject's pose at the future time indicated in the Scanner Timing Information. The Adjusted Motion Information corresponding to the Scanner Timing Information is passed to the Scan Control and MR Pulse Sequence Generation element.

The Scan Control and MR Pulse Sequence Generation element receives Adjusted Motion Information for corresponding Scanner Timing Information and generates Adapted Pulse Sequence Parameters, which are executed on the MR Scanner, thus realizing RGR-based adaptive MR imaging and spectroscopy.

Essentially, the motion tracking information is used to predict the change in pose of the patient due to movement, and the predicted pose is sent to the scanner, which then dynamically adjusts the pose of each scan plane or volume to compensate for the patient's movement.

Comparing the flow chart of FIG. 2 with the flow chart of FIG. 3, in the preferred embodiment, the "Motion Filtering and Prediction" routines run on the RGR Processing Computer 50, and there is no separate computer for the optional motion filtering and prediction calculations, which are relatively minor from the standpoint of computer burden. In alternative embodiments, the Motion Filtering and Prediction routines could run on a separate computer (or hardware or software), or on the Scanner Control and Processing Computer.

Figure 4:
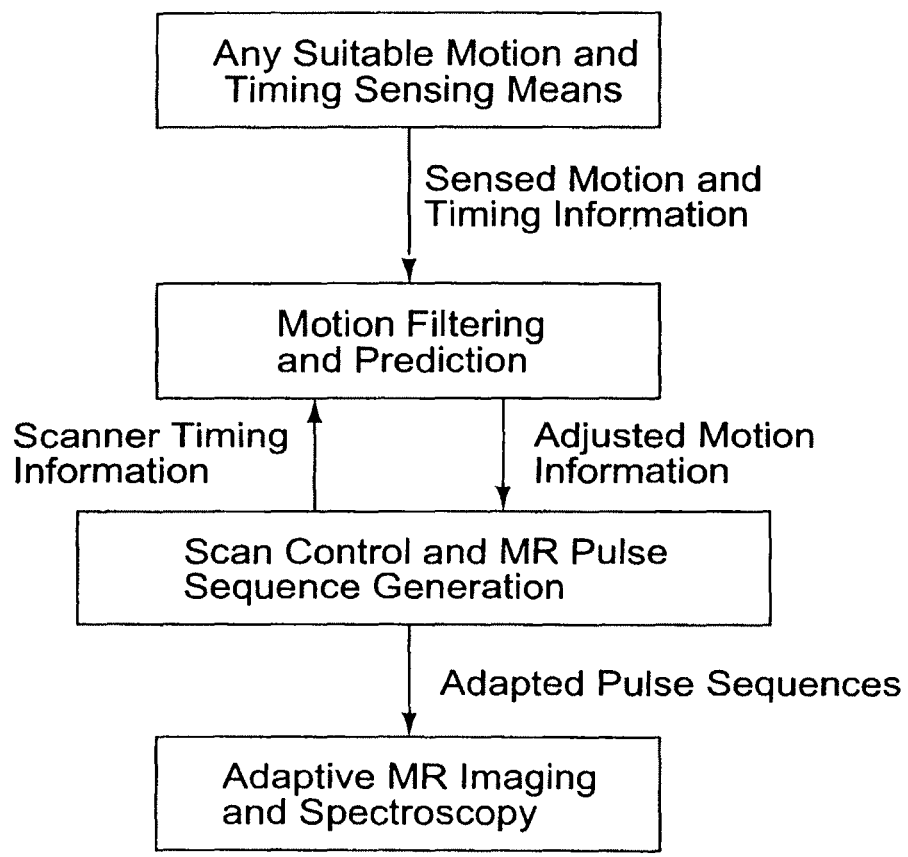
FIG. 4 is a flow chart of steps for adaptive MR imaging in an alternative embodiment, incorporating motion sensing by any suitable means such as MR scan analysis and optional motion filtering and prediction.

FIG. 4 illustrates an alternative embodiment of the invention. In this embodiment, any suitable motion and timing sensing means is used, including, but not limited to, motion sensing by image analysis, as is known in the prior art, such as commercially available Stereo Vision systems. The innovation in this embodiment is to employ a Motion Filtering and Prediction element to analyze a plurality of recent RGR Motion and Timing Information as well as Scanner Timing information to produce Adjusted Motion Information, which is the best estimate of the subject pose at the time indicated in the Scanner Timing Information. The Adjusted Motion Information is passed to the Scan Control and MR Pulse Sequence Generation element.

The Scan Control and MR Pulse Sequence Generation element receives Adjusted Motion Information and generates Adapted Pulse Sequence Parameters, which are sent to the MR Scanner and executed, thus realizing RGR-based adaptive MR imaging and spectroscopy.

Figure 5:
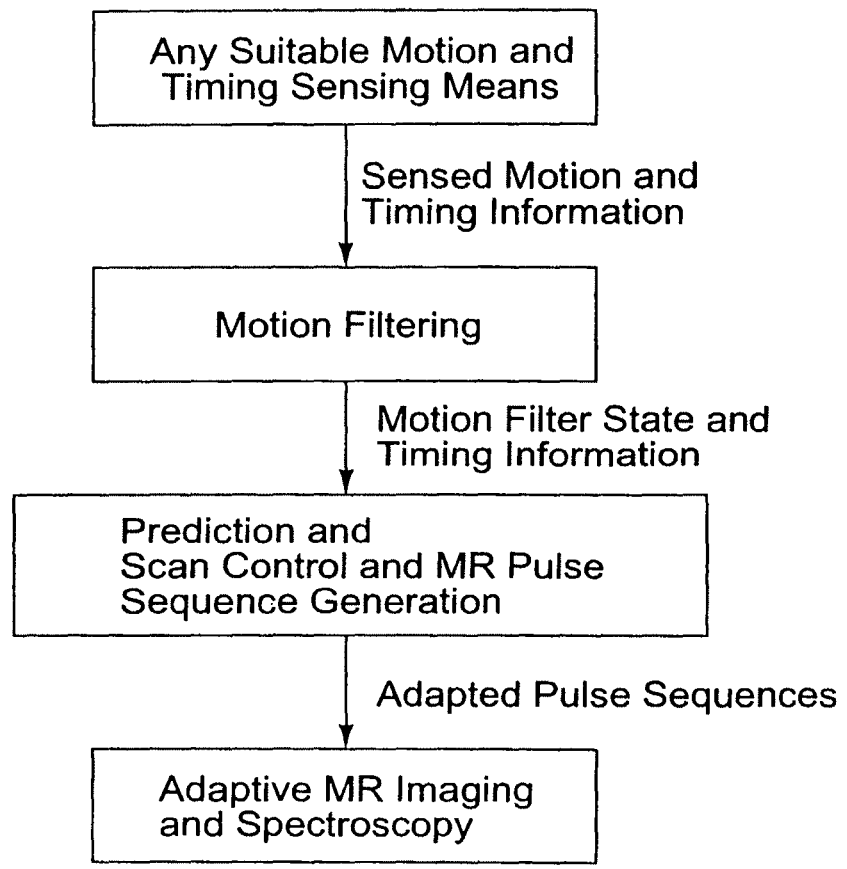
FIG. 5 is a flow chart of steps for adaptive MR imaging in an alternative embodiment in which the motion filtering is performed separately.

Yet another embodiment is illustrated in FIG. 5. In this alternative embodiment the Motion Filtering calculations are executed by a Motion Tracking system computer, and the Motion Filter State and Timing Information are transferred to the Scanner Control and Processing Computer. The Prediction portion of the Motion Filtering and Prediction algorithm utilizes the Motion Filter State and Timing Information, as well as Scanner Timing Information that is internal to the Scanner Control and Processing Computer, to predict the subject pose at the time indicated in the Scanner Timing Information.

Figure 7:
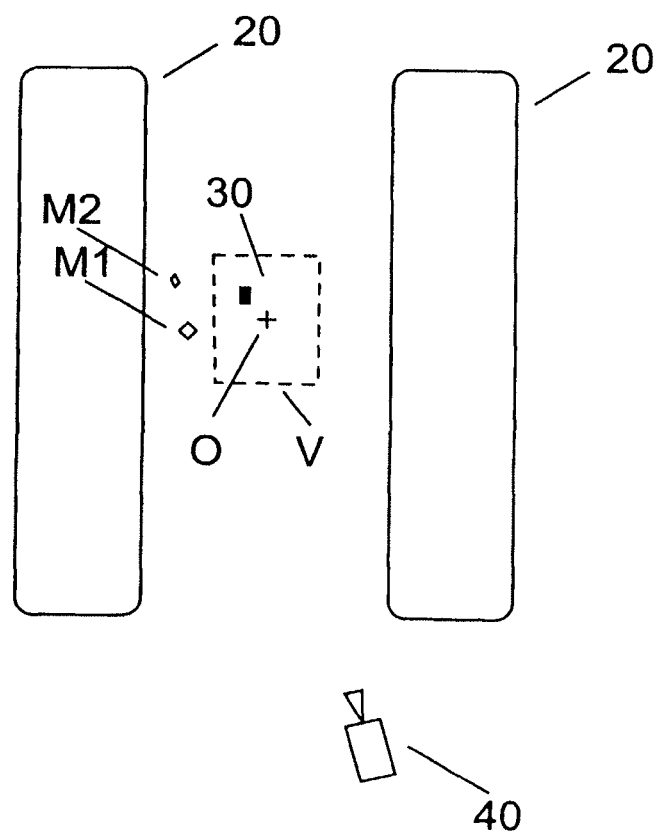
FIG. 7 is a top plan view of the embodiment of FIG. 6.
Figure 8:
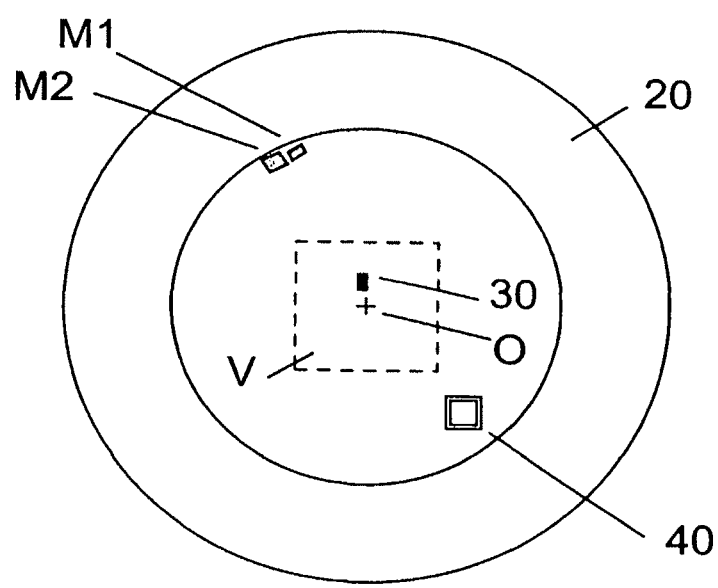
FIG. 8 is a back elevational view of the embodiment of FIG. 6.

FIGS. 6 to 8 show various views of the presently preferred embodiment of the RGR-based adaptive MR imaging and spectroscopy system. Each view illustrates the relationship of the scanning volume V (here, the bore of an MR Scanner magnet), detector (here, a camera 40) and object orientation marker 30 (preferably an RGR tag, target or marker). The camera 40 is preferably outside and behind the scanner magnet 20.

Also seen in the figures are optional mirrors M1 and M2, each with or without a separate optional RGR, which are used to allow the camera 40 to be placed outside a direct line of sight with the object orientation marker 30, to avoid blockage and for other reasons. Considering the openings that are typically available in the coil surrounding the subject's head during MR scans, the top position point-of-view offers superior measurement accuracy. FIG. 6 also shows the position of the origin 0 of the medical imaging coordinate frame.

In one preferred embodiment of the invention, if the patient requires a brain or head scan, one RGR target 30 (the "mobile RGR tag") is affixed to the side of the nose of the patient. This particular location has the advantage of being relatively immobile during head movements. However, a person knowledgeable in the art will recognize that the mobile RGR tag may also be affixed to other parts of the body.

In one preferred embodiment of the invention, a single mirror is used to observe the mobile RGR target from the camera. In another preferred embodiment of the invention, a mirror orientation marker (a "stationary marker"), preferably an RGR tag, is mounted on the single mirror. This mirror RGR tag is directly visible from the camera, and is being analyzed continuously in addition to the mobile RGR on the organ of interest. Analyzing the pose of the mirror RGR makes it possible to ensure the "internal calibration" of the RGR tracking system, i.e. to ensure the relative position of the camera and mirror are known accurately.

In yet another embodiment of the invention, two or more mirrors are used to observe the mobile RGR from the camera. The mirrors are arranged such that the reflected image of the mobile RGR is visible to the camera in all of them. Having two or more mirrors makes it possible to observe the mobile RGR on the patient, and determine the patient pose, even if one of the views is obstructed.

In another preferred embodiment of the invention, a single camera observes the mobile RGR on the subject directly as well as indirectly, creating two lines of sight. The camera is pointed towards a semi-transparent mirror (or prism) that splits the optical path into two. The direct, non-reflective optical path is pointed towards the mobile RGR, allowing a direct line of sight. The reflective optical path leads towards a second mirror or prism (fully reflective), and is redirected towards the RGR. One or both of the two mirrors or prisms can be equipped with RGRs, to enable internal calibration. This configuration allows mounting of the camera inside the MRI scanner bore, and provides the same advantages as the two-mirror/stationary RGR system disclosed herein.

In yet another embodiment of the invention, a single-camera is pointing directly towards the mobile RGR. However, half the field-of-view of the camera is obstructed by a mirror or prism. The reflected optical path leads towards a second mirror or prism that redirects the optical path towards the RGR. One or both of the two mirrors or prisms can be equipped with RGRs, to enable internal calibration. This configuration allows mounting of the camera inside the MRI scanner bore, and provides the same advantages as the two-mirror/stationary RGR system disclosed herein.

In another preferred embodiment of the invention, additional mirror orientation markers, preferably stationary RGR tags, are mounted on each of two or more mirrors, or on brackets holding one or more of the mirrors. The mirrors and stationary RGR tags are arranged such that the mobile RGR tag and all the stationary RGR tags are visible from the camera. All stationary RGR tags, as well as the mobile RGR tag on the patients, are being analyzed continuously. It would be expected that the accuracy of optical measurements would suffer if more optical elements are introduced into the measurement system because of the need to maintain more elements in alignment. However, by analyzing all the information from all RGRs simultaneously, this particular embodiment of the invention results in a dramatic and unexpected improvement in accuracy of the tracking system, such that the tracking accuracy is unexpectedly approximately 10-fold greater than that of a conventional stereo-vision system accuracy of the tracking system, such that the tracking accuracy is unexpectedly approximately 10-fold greater than that of a conventional stereo-vision system.

In another embodiment of this RGR-based adaptive MR imaging and spectroscopy system, the tracking camera is installed inside the MR magnet and observes the mobile RGR target either directly or via one or more mirrors (each with or without its own stationary RGR). In this instance, the camera needs to be shielded to avoid interference with the MR measurement system.

Figure 9:
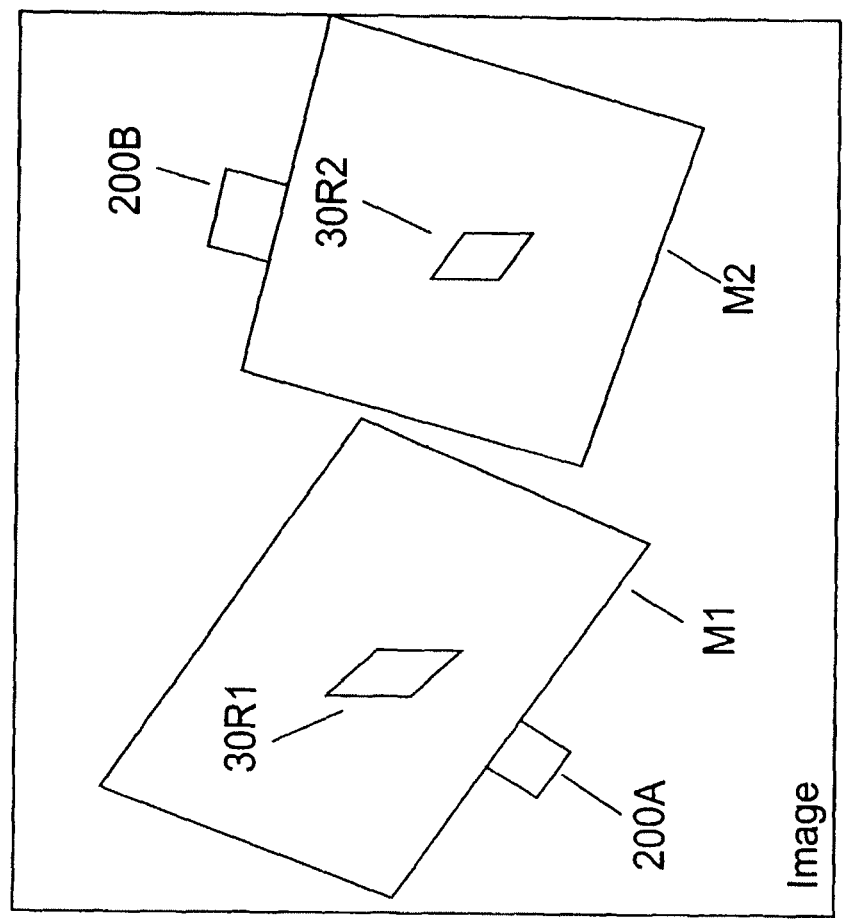
FIG. 9 is a camera view, showing the mirrors and object orientation markers in the camera in the embodiment of FIG. 6, and also showing placement of optional RGRs on mirrors.

FIG. 9 exemplifies an RGR camera view which would be typical in the preferred embodiment with two mirrors M1 and M2. Optionally, mirror orientation markers 200A and 200B can be attached to the mirrors M1 and M2. The RGR Camera is arranged to produce an image of the mirrors, and the mirrors are arranged so that the mobile RGR tag is reflected in both of the mirrors and two reflected images of the mobile RGR tag 30R1 and 302 are visible to the camera. Two (or more) mirrors are used to obtain multiple views of the RGR target in a single image. Optionally, the mirror orientation markers 200A and 200B also can be viewed directly by the camera.

While the use of two or more mirrors, each with its optional associated stationary mirror RGR, may seem more cumbersome and error-prone than a single-mirror configuration, it provides several important and unexpected advantages. First, the multiple views of the mobile RGR target provide multiple lines of sight. One advantage of obtaining multiple views of the RGR target is that at least one view will remain clear and available for motion tracking, even if another view is obscured. A view can be obscured by, for example, a portion of the head coil that surrounds the head of the subject during functional MR scanning. A second advantage of obtaining multiple views of the mobile RGR target is an unexpected and dramatic improvement in the accuracy of the motion tracking system, such that the 2-mirror system is approximately 10 times more accurate than a stereovision tracking system. Therefore, a multi-mirror multi-RGR system provides substantial advantages that cannot be reproduced with other typical motion tracking systems, such as a stereovision system.

While the use of two or more mirrors, each with its optional associated stationary mirror RGR, may seem more cumbersome and error-prone than a single-mirror configuration, it provides several important and unexpected advantages. First, the multiple views of the mobile RGR target provide multiple lines of sight. One advantage of obtaining multiple views of the RGR target is that at least one view will remain clear and available for motion tracking, even if another view is obscured. A view can be obscured by, for example, a portion of the head coil that surrounds the head of the subject during functional MR scanning. A second advantage of obtaining multiple views of the mobile RGR target is an unexpected and dramatic improvement in the accuracy of the motion tracking system, such that the 2-mirror system is approximately 10 times more accurate than a stereovision tracking system. Therefore, a multi-mirror multi-RGR system provides substantial advantages that cannot be reproduced with other typical motion tracking systems, such as a stereovision system.

Yet another preferred embodiment of the invention involves a combination of any of the embodiments of the RGR-based tracking system described above, with a system that makes it possible to automatically and continuously calibrate the RGR-tracking system ("auto-tuning"), in order to eliminate the effect of drift and other calibration inaccuracies in the camera system. As noted above, because the required co-registration accuracy (between the Medical imaging system and the tracking system) is very high (on the order of 0.1 mm and 0.1 degree for Medical Imaging) and because the elements of prior art measurement systems can be widely separated (for example, by several meters for Magnetic Resonance imaging), thennal drift, vibration and other phenomena can cause the alignment ("co-registration") between the motion tracking system coordinate frame c and scanning system coordinate frame M to change over time. The prior art has no means to track or correct for these slow changes while the medical imaging system is in service, imaging patients. The error which accumulates in the co-registration is a severe problem for motion compensation in medical imaging using an external motion tracking system. Time on a medical imaging system is limited and expensive, and removing patients and conducting periodic recalibration with a specialized calibration tool or target is prohibitively expensive.

Figure 10:
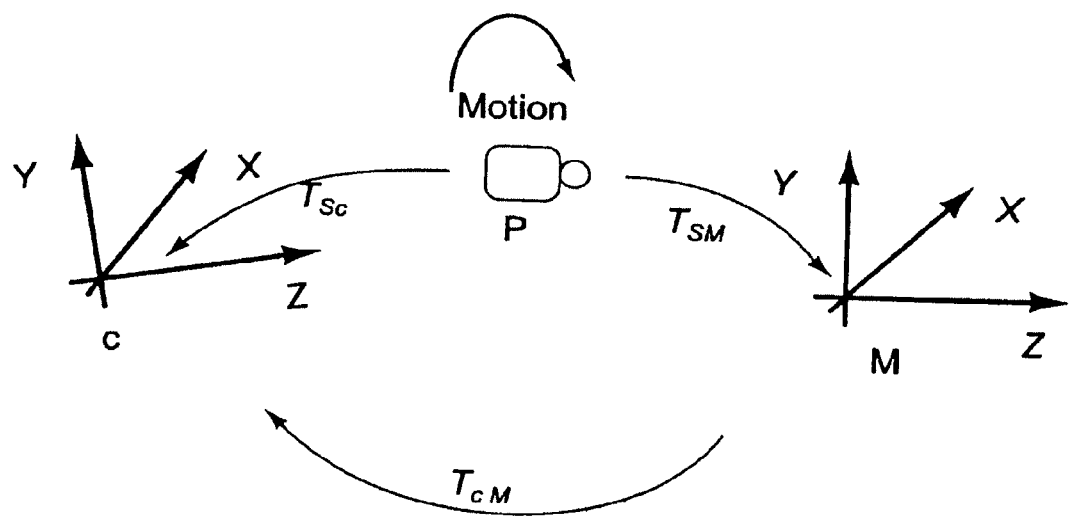
FIG. 10 is a conceptual diagram illustrating that motion of the subject can be determined in both the coordinate frames of the motion tracking system and of the MR machine.

FIG. 10 illustrates the coordinate frames of a system for real-time adaptive Medical Imaging. The system comprises a Motion Tracking System (preferably tracking motion in real time), such as the RGR tracking system, which produces timely measurements of the subject pose within a motion tracking coordinate frame 'c'.

Simultaneously, the subject is imaged by a Medical Imaging system, such as an MR Scanner, which operates within a medical imaging coordinate frame 'M'. Improved medical images are obtained if (real-time) Motion Information is available to the Medical Imaging system, but the Motion Information must be accurately translated (or transformed) from the real-time motion tracking system (coordinate frame 'c,') to the coordinate frame 'M' of the Medical Imaging system. The motion tracking system is considered "calibrated" with respect to the MR system if the mathematical transformation leading from one coordinate system to the other coordinate system is known. However, the calibration (or alignment) of the two coordinate systems can be lost, introducing inaccuracies, due to drift over time because of various factors, including heat and vibration.

Motion Information is transformed from frame 'c' to frame 'M' by a "coordinate transformation matrix", or "Co-registration transformation $T_{c \leftarrow M}$." The "coordinate transformation matrix" converts or transforms motion information from one coordinate frame to another, such as from the motion tracking coordinate frame c to the medical imaging coordinate frame M. Loss of calibration due to drift, as well as other calibration inaccuracies, will result in a change over time of the coordinate transformation matrix, which in turn will lead to errors in the tracking information.

U.S. Pat. No. 6,044,308, incorporated herein by reference, describes the AX=XB method of coordinate transformations. This patent teaches the use of the AX=XB method for determining the transformation from a tool coordinate frame to a robot coordinate frame, where the tool moves with the end effector of the robot over the course of many hours or days) due to temperature changes, vibrations and other effects. This variation introduces error into the Transformed Real-time Motion Information for real-time adaptive Medical Imaging (over the course of many hours or days) due to temperature changes, vibrations and other effects. This variation introduces error into the Transformed Real-time Motion Information for real-time adaptive Medical Imaging.

Figure 11:
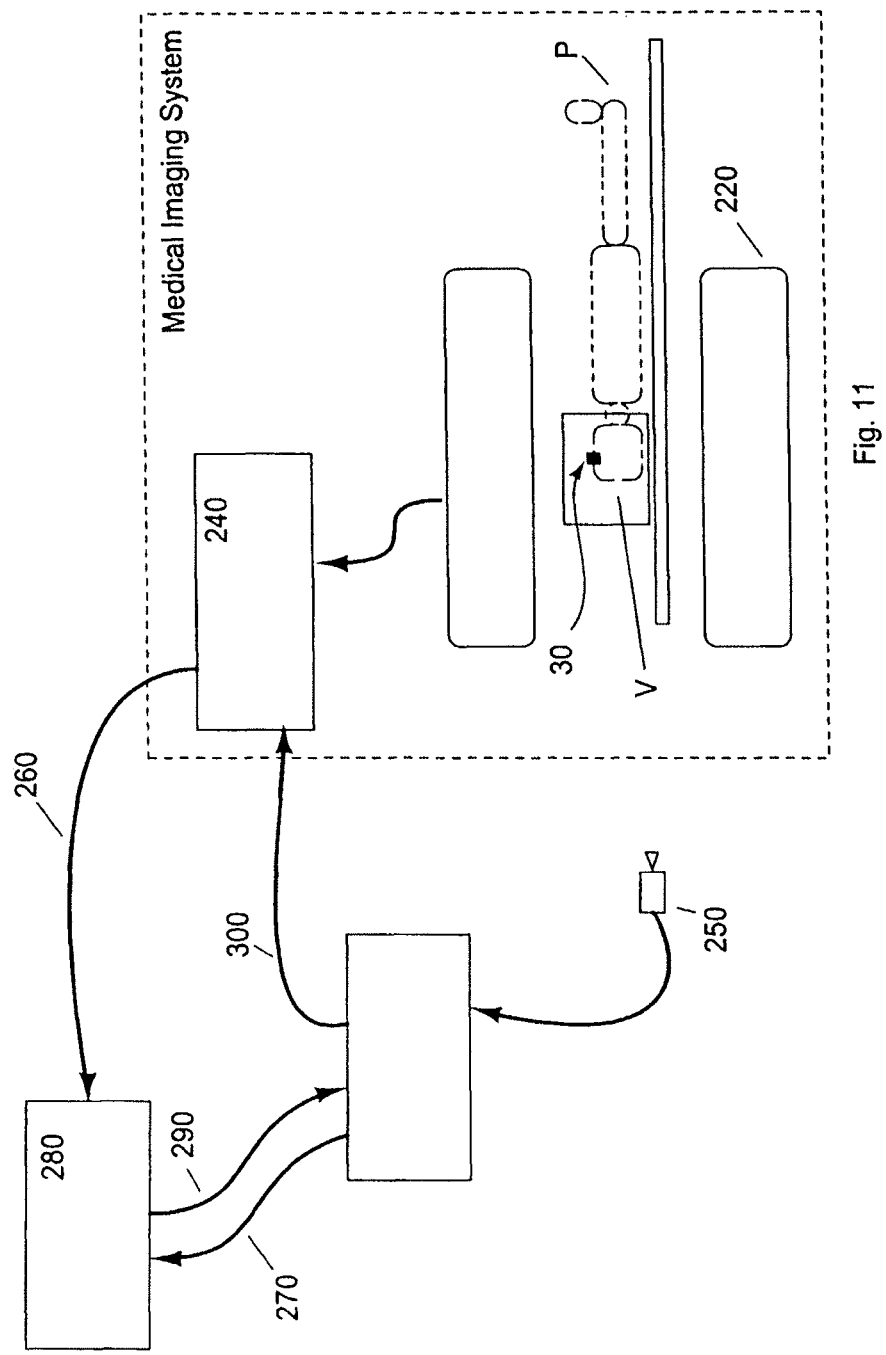
FIG. 11 is a conceptual flow chart illustrating a system for continuous tuning ("Auto-tuning") of the co-registration transformation between a Motion Tracking system and a Medical Imaging system.

FIG. 11 illustrates the elements of an embodiment of the system for Auto-tuning for automatic and continuous determination of the co-registration transformation between a Motion Tracking system and a Medical Imaging system. A patient P is imaged inside a Medical Imaging system comprising a medical imaging device 220 and a Medical Imaging and Control & Processing Element 240. Simultaneously, a Motion Tracking system comprising a motion tracking detector 250, and a motion tracking processing element, such as any embodiment of the RGR-tracking system, makes real-time motion measurements. Using the co-registration transformation $T_{c \leftarrow M}$, the real-time Motion Information is transformed from the Motion Tracking system coordinate frame to the Medical Imaging system coordinate frame. Concurrent with the processes described above, Delayed Medical Image Motion Information 260 and Delayed Motion Tracking Motion Information 270 is supplied to the Co-registration Auto-tuning Element 280. This information is delayed because the Medical Image Motion Information is only available in delayed form and typically much less frequently than the information from the tracking system. For instance, ultra-fast MRI scanning sequences, such as echo planar imaging (EPI), make it possible to scan the entire head, or other organs of interest, every few seconds. From each of these volumetric data sets, it is possible to determine head position and rotation, with a time resolution of a few seconds. Alternatively, navigator scans can provide position information a few times each second. Displacements of the subject are recorded from both sources of Motion Information, i.e. from the RGR motion tracking system, as well as an MRI scanner, e.g. registration of EPI-volumes or navigator scans. By comparing these measured displacements, the Co-registration Auto-tuning Element adjusts the coordinate transformation matrix $T_{c \leftarrow M}$ to compensate for changes in the co-registration of the Motion Tracking system and the Medical Imaging system. The updated value 290 of the coordinate transformation matrix $T_{c \leftarrow M}$ is repeatedly generated and supplied to the Motion Tracking system for use in transforming the Real-time Motion Information to Medical Imaging system coordinates 300.

In the preferred embodiment of the auto-tuning system, each of the three processing elements is implemented as computer software running on a separate computer. Those skilled in the art of real-time computer systems will see that other configurations are possible, such as all processing elements running on a single computer, or two or more computers working in coordination to realize one of the processing elements.

With automatic and continuous tuning of the co-registration transformation, the real-time Motion Information produced by the Motion Tracking System is accurately transformed into Medical Imaging system coordinates, so as to be usable by the Medical Imaging system for real-time adaptive Medical Imaging, even in the presence of inevitable drift and other calibration inaccuracies arising from variations over time of the relative position and orientation of the Motion Tracking and Medical Imaging coordinate frames.

Figure 12:
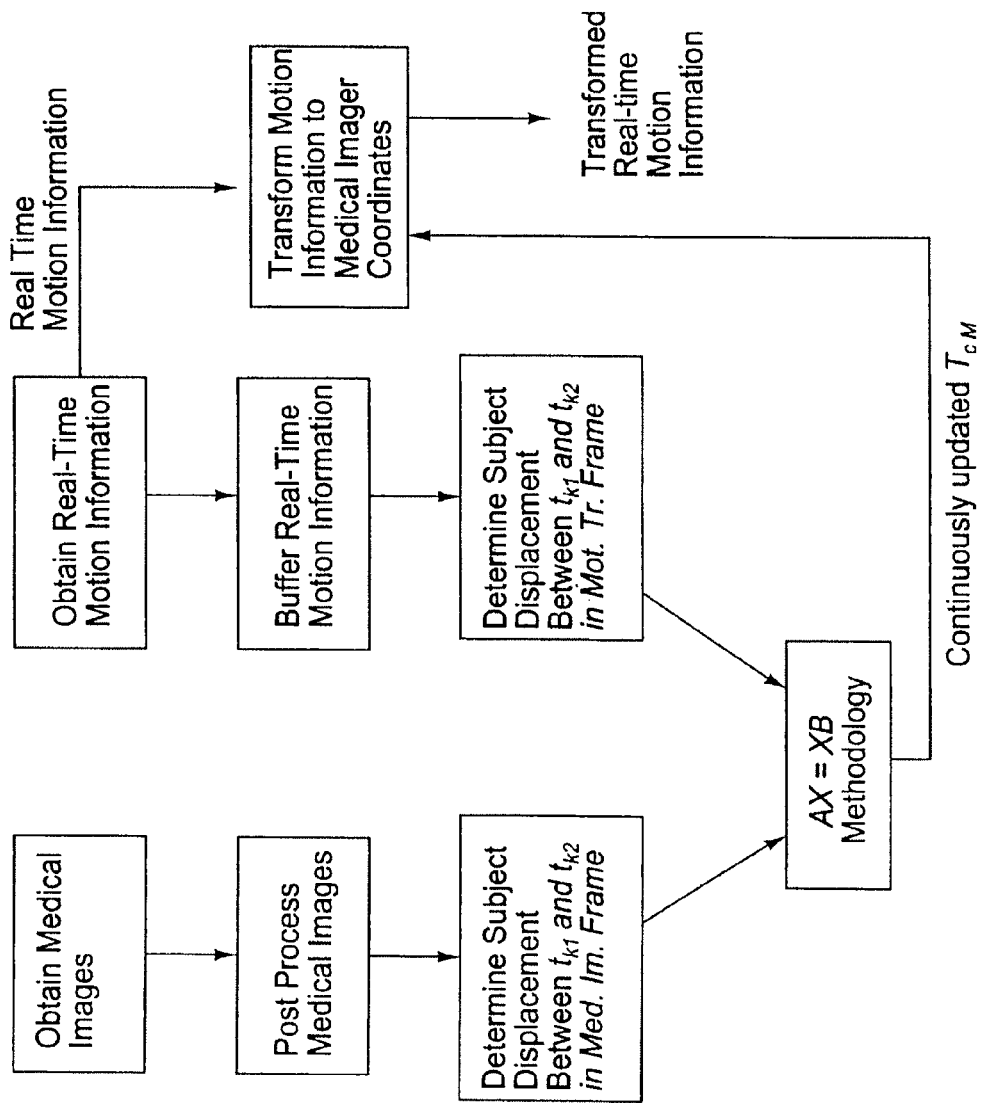
FIG. 12 is a flow chart of steps for Auto-tuning for automatic and continuous adjustment of the Co-registration Transformation between a Motion Tracking system and a Medical Imaging system.
Figure 13:
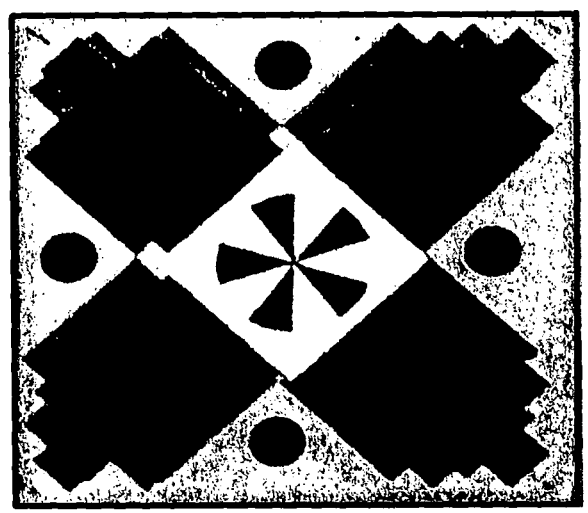
FIG. 13 is a drawing of an RGR target.

FIG. 12 provides a flow chart of the steps for Auto-tuning for automatic and continuous co-registration of a Motion Tracking system (for instance any embodiment of the RGR-tracking system described above), with a Medical Imaging system. The Medical Imaging system obtains Medical Images. These are analyzed by post processing using prior art methods to produce Delayed Medical Image Motion Information in the form of the measured displacement of the imaging subject (e.g., the patient's head) between two times, tk1 and tk2. This displacement is measured in the Medical Imaging system coordinate frame.

Concurrently, the Motion Tracking system is used to obtain real-time Motion Information, which may be transformed into the Medical Imaging system coordinates to provide for real-time adaptive Medical Imaging. The Motion Tracking Motion Information is also stored in a buffer. Past values of the Motion Tracking Motion Information from the buffer are used to determine a second displacement of the imaging subject as detected by the Motion Tracking system, between the two previously mentioned times, tk1 and tk2. This second displacement is measured in the Motion Tracking system coordinate frame.

The displacement determined by post processing of the Medical Images and the displacement determined from the buffered Motion Tracking Motion Information are passed to the registration routine based on an approach labeled as "A X=X B methodology", which is known to the prior art. See, for example, Park, F. C. and B J. Martin, "Robot Sensor Calibration: Solving AX=XB on the Euclidean Group", *IEEE Transactions on Robotics and Automation*, 1994. 10(5): p. 717-721; Angeles, J., G. Soucy, and F. P. Ferrie, "The online solution of the hand-eye problem", *IEEE Transactions on Robotics and Automation*, 2000. 16(6): p. 720-731; Chou J C K, Kamel M., "Finding the Position and Orientation of a Sensor on a Robot Manipulator Using Quaternions", *The International Journal of Robotics Research* 1991; 10:240-254; Shiu Y C, Ahmad S., "Calibration of Wrist-Mounted Robotic Sensors by Solving Homogeneous Transform Equations of the Form AX=XB", *IEEE Transactions on Robotics and Automation* 1989; 5:16-29; Tsai R Y, Lenz R K, "A New Technique for fully autonomous and efficient 3D robotics hand/eye calibration", *IEEE Journal of Robotics and Automation* 1989; 3:345-358; Wang C C, "Extrinsic Calibration of a Vision Sensor Mounted on a Robot", *IEEE Transactions on Robotics and Automation* 1992; 8: 161-175, all of which are incorporated herein by reference.

Using this method, the co-registration $T_{c \leftarrow M}$ is updated. Therefore, by continuously updating the co-registration information, gradual and inevitable drifts and other calibration inaccuracies in the alignment of the Motion Tracking system and the Medical Imaging system coordinate frames are corrected and accurate adaptive compensation for subject motion is achieved even in the presence of drift and other calibration inaccuracies in the equipment.

Persons knowledgeable in the art will recognize that the auto-tuning technique described in this disclosure may also utilize motion information from multiple (more than 2) time points, for instance in the form of filtering, which will generally increase the accuracy of the auto-tuning procedure.

Persons knowledgeable in the art will recognize that the techniques described in this disclosure may also be applied to medical imaging techniques other than MRI, such as PET, SPECT, CT, or angiographic scanning.

The optimal embodiment of the RGR-based adaptive motion compensation system involves (1) the RGR system shown in FIGS. 6-9, (2) two or more observation mirrors, each optionally with its own stationary RGR, and (3) the auto-tuning system.

While the present invention has been disclosed in connection with the presently preferred best modes described herein, it should be understood that there are other embodiments which a person of ordinary skill in the art to which this invention relates would readily understand are within the scope of this invention. For example, the present invention shall not be limited by software, specified scanning methods, target tissues, or objects. For a further example, instead of using a camera or other optical imaging device to determine an object's pose, alternative detectors of pose can be used, including non-imaging detectors and non-optical detectors, such as magnetic detectors or polarized light detectors. Accordingly, no limitations are to be implied or inferred in this invention except as specifically and explicitly set forth in the attached claims.

INDUSTRIAL APPLICABILITY

This invention can be used whenever it is desired to compensate for motion of a subject, especially while taking a long duration scan.

What is claimed is:

1. A magnetic resonance image recording and tracking system for use during a magnetic resonance examination by a magnetic resonance scanner, comprising:
   a wall of a scanner bore of a magnetic resonance magnet;
   a receiving area that is at least enclosed partially by the wall;
   a small camera positioned on or in the wall of the scanner bore, the small camera configured to periodically image a marker in the receiving area; and
   a tracking system configured to analyze images generated by the small camera to determine changes in position of the marker, and to generate tracking data for use by the magnetic resonance scanner to dynamically adjust scans to compensate for the changes in position of the marker.

2. The magnetic resonance image recording and tracking system of claim 1, further comprising a second camera positioned on or in the wall of the scanner bore, the second camera configured to periodically image the marker in the receiving area.

3. The magnetic resonance image recording and tracking system of claim 2, wherein the second camera is configured to continuously image a second marker in the receiving area.

4. The magnetic resonance image recording and tracking system of claim 2, wherein the small camera and the second camera are each configured to view the marker along a different line of sight.

5. The magnetic resonance image recording and tracking system of claim 1, wherein the small camera is configured to continuously image the marker in the receiving area.

6. The magnetic resonance image recording and tracking system of claim 1, wherein the marker is an object orientation marker.

7. The magnetic resonance image recording and tracking system of claim 6, wherein the object orientation marker is configured to indicate orientation in six degrees of freedom.

8. The magnetic resonance image recording and tracking system of claim 6, wherein the object orientation marker is a retro-grate reflector marker.

9. The magnetic resonance image recording and tracking system of claim 1, wherein the tracking system comprises a computer processor and an electronic memory.

10. The magnetic resonance image recording and tracking system of claim 1, wherein the small camera is shielded to avoid interference with the magnetic resonance scanner.

11. A magnetic resonance image recording and tracking system for use during a magnetic resonance examination by a magnetic resonance scanner, comprising:
   a detector configured for positioning on or in a wall of a scanner bore of a magnetic resonance magnet, the wall at least partially enclosing a receiving area that is configured to receive a subject for scanning by the magnetic resonance scanner, the detector configured to image a marker coupled to the subject in the receiving area; and
   a tracking system configured to analyze images generated by the detector to determine changes in position of the marker, and to generate tracking data for use by the magnetic resonance scanner to dynamically adjust scans to compensate for the changes in position of the marker, wherein the tracking system comprises a computer processor and electronic memory.

12. The magnetic resonance image recording and tracking system of claim 11, wherein the detector comprises a camera.

13. The magnetic resonance image recording and tracking system of claim 11, wherein the detector comprises at least two detectors, the at least two detectors each configured to view the marker along a different line of sight.

14. The magnetic resonance image recording and tracking system of claim 11, wherein the detector is configured to continuously image the marker in the receiving area.

15. The magnetic resonance image recording and tracking system of claim 11, wherein the marker is an object orientation marker.

16. The magnetic resonance image recording and tracking system of claim 15, wherein the object orientation marker is configured to indicate orientation in six degrees of freedom.

17. The magnetic resonance image recording and tracking system of claim 15, wherein the object orientation marker is a retro-grate reflector marker.

18. The magnetic resonance image recording and tracking system of claim 11, wherein the detector is shielded to avoid interference with the magnetic resonance scanner.

19. The magnetic resonance image recording and tracking system of claim 11, wherein the detector is configured to directly image the marker coupled to the subject in the receiving area.

20. The magnetic resonance image recording and tracking system of claim 11, further comprising at least one mirror, wherein the detector is configured to indirectly image through the mirror the marker coupled to the subject in the receiving area.

21. A magnetic resonance image recording and tracking system for use during a magnetic resonance examination by a magnetic resonance scanner, comprising:
   a wall of a scanner bore of a magnetic resonance magnet;
   a receiving area that is at least enclosed partially by the wall;
   a camera positioned in the wall of the scanner bore, the camera configured to periodically image a marker in the receiving area; and
   a tracking system configured to analyze images generated by the camera to determine changes in position of the marker, and to generate tracking data for use by the magnetic resonance scanner to dynamically adjust scans to compensate for the changes in position of the marker, the tracking system comprises a computer processor and electronic memory.

22. The magnetic resonance image recording and tracking system of claim 21, further comprising a second camera positioned in the wall of the scanner bore, the second camera configured to periodically image the marker in the receiving area.

23. The magnetic resonance image recording and tracking system of claim 22, wherein the second camera is configured to continuously image a second marker in the receiving area.

24. The magnetic resonance image recording and tracking system of claim 22, wherein each of the cameras are configured to view the marker along a different line of sight.

25. The magnetic resonance image recording and tracking system of claim 21, wherein the camera is configured to continuously image the marker in the receiving area.

26. The magnetic resonance image recording and tracking system of claim 21, wherein the marker is an object orientation marker.

27. The magnetic resonance image recording and tracking system of claim 26, wherein the object orientation marker is configured to indicate orientation in six degrees of freedom.

28. The magnetic resonance image recording and tracking system of claim 26, wherein the object orientation marker is a retro-grate reflector marker.

29. The magnetic resonance image recording and tracking system of claim 21, wherein the camera is shielded to avoid interference with the magnetic resonance scanner.

30. The magnetic resonance image recording and tracking system of claim 21, wherein the camera is configured to directly image the marker in the receiving area.

31. The magnetic resonance image recording and tracking system of claim 21, further comprising at least one mirror, wherein the camera is configured to indirectly image through the mirror the marker in the receiving area.

* * * * *

UNITED STATES PATENT AND TRADEMARK OFFICE
CERTIFICATE OF CORRECTION

| | |
|---|---|
| PATENT NO. | : 9,138,175 B2 |
| APPLICATION NO. | : 14/698350 |
| DATED | : September 22, 2015 |
| INVENTOR(S) | : Thomas Michael Ernst et al. |

It is certified that error appears in the above-identified patent and that said Letters Patent is hereby corrected as shown below:

On the title page

In column 1 (page 6, item 56) at line 6, Under Other Publications, change ""Hybrind" to --"Hybrid--.

In column 1 (page 6, item 56) at line 20, Under Other Publications, change "Breain"," to --Brain",--.

In column 1 (page 6, item 56) at line 27, Under Other Publications, change "magnetric" to --magnetic--.

In column 1 (page 6, item 56) at line 53, Under Other Publications, change "Continous" to --Continuous--.

In column 2 (page 6, item 56) at line 32, Under Other Publications, change "AX-XB" to --AX=XB--.

In the specification

In column 1 at line 63, Change "know" to --known--.

In column 3 at line 11, Change "aI," to --al.,--.

In column 4 at line 2, Change "aI," to --al.,--.

In column 4 at line 13, Change "(lion" to --("on--.

In column 4 at line 63, Change "1I100th" to --1/100th--.

In column 5 at line 30, Change "em" to --cm--.

In column 5 at line 47, Change "Information)," to --Information).--.

In column 11 at line 7, Change "Information," to --Information.--.

In column 13 at line 31, Change "302" to --30R2--.

Signed and Sealed this
Seventh Day of June, 2016

Michelle K. Lee
*Director of the United States Patent and Trademark Office*

In columns 13-14 at lines 54-67 (Col. 13) 1-4 (Col. 14), Below "system." delete "While the use. . . system."(Repeated Paragraph)

In column 14 at line 17, Change "thennal" to --thermal--.